(12) United States Patent
Vidal et al.

(10) Patent No.: US 7,642,360 B2
(45) Date of Patent: Jan. 5, 2010

(54) COMPOSITION FOR DYEING KERATINOUS FIBERS COMPRISING AT LEAST ONE DIAMINO-N,N-DIHYDROPYRAZOLONE DERIVATIVE

(75) Inventors: Laurent Vidal, Paris (FR); Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/898,438

(22) Filed: Sep. 12, 2007

(65) Prior Publication Data

US 2008/0071092 A1 Mar. 20, 2008

Related U.S. Application Data

(62) Division of application No. 10/999,999, filed on Dec. 1, 2004, now Pat. No. 7,285,137.

(60) Provisional application No. 60/527,778, filed on Dec. 9, 2003, provisional application No. 60/549,535, filed on Mar. 4, 2004.

(30) Foreign Application Priority Data

Dec. 1, 2003 (FR) .................................. 03 50950
Feb. 18, 2004 (FR) .................................. 04 50297

(51) Int. Cl.
*C07D 231/54* (2006.01)
(52) U.S. Cl. .................. 548/363.1; 548/366.1
(58) Field of Classification Search ............. 548/356.1, 548/366.1, 367.4, 367.7, 369.4, 370.1, 363.1
See application file for complete search history.

(56) References Cited

U.S. PATENT DOCUMENTS

| | | | |
|---|---|---|---|
| 3,012,884 | A | 12/1961 | de Ramaix et al. |
| 4,128,425 | A | 12/1978 | Greenwald |
| 5,061,289 | A | 10/1991 | Clausen et al. |
| 5,500,439 | A * | 3/1996 | Ulrich et al. ............. 514/404 |
| 5,718,731 | A | 2/1998 | Loewe et al. |
| 6,660,046 | B1 | 12/2003 | Terranova et al. |

FOREIGN PATENT DOCUMENTS

| | | |
|---|---|---|
| CH | 421 343 | 9/1966 |
| DE | 1 959 009 | 12/1970 |
| DE | 38 43 892 A1 | 6/1990 |
| DE | 196 19 112 A1 | 11/1997 |
| EP | 0 873 745 A2 | 10/1998 |
| EP | 1 250 909 A1 | 10/2002 |
| GB | 1 005 233 | 9/1965 |
| JP | 2002-535312 | 10/2002 |

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
English language Derwent Abstract of DE 1 959 009, Dec. 3, 1970.
English language Derwent Abstract of DE 196 19 112 A1, Nov. 13, 1997.
English language Derwent Abstract of EP 0 873 745 A2, Oct. 28, 1998.
English language Derwent Abstract of EP 1 250 909 A1, Oct. 23, 2002.
STIC Search Report dated Dec. 13, 2006.
Helvetica Chimica Acta., vol. XXXIII, Fasciculus V (1950), No. 152 pp. 1183-1194.
English translation of Helvetica Chimica Acta., vol. XXXIII, Fasciculus V (1950), No. 152, pp. 1183-1194.
Notice of Rejection in the counterpart Japanese Application No. 2004-348020 mailed Dec. 6, 2005.

* cited by examiner

*Primary Examiner*—Kamal A Saeed
*Assistant Examiner*—Samantha L Shterengarts
(74) *Attorney, Agent, or Firm*—Finnegan, Henderson, Farabow, Garrett & Dunner, LLP

(57) ABSTRACT

Disclosed herein are a composition for dyeing keratinous fibers, for example, human keratinous fibers such as hair, comprising at least one oxidation base chosen from diamino-N,N-dihydropyrazolone derivative and a method using the composition. Further disclosed herein are amino-N,N-dihydropyrazolone derivatives and the addition salts thereof and diamino-N,N-dihydropyrazolone derivatives and the addition salts thereof, as well as the methods for preparing these compounds.

17 Claims, No Drawings

COMPOSITION FOR DYEING KERATINOUS FIBERS COMPRISING AT LEAST ONE DIAMINO-N,N-DIHYDROPYRAZOLONE DERIVATIVE

This application is a division of application Ser. No. 10/999,999, filed Dec. 1, 2004, now U.S. Pat. No. 7,285,137 and claims the benefit of U.S. Provisional Application No. 60/527,778, filed Dec. 9, 2003, and U.S. Provisional Application No. 60/549,535, filed Mar. 4, 2004, all of which are incorporated herein by reference. This application also claims benefit of priority under 35 U.S.C. §119 of French applications 04/50297, filed Feb. 18, 2004, and 03/50950, filed Dec. 1, 2003, both of which are also incorporated herein by reference.

Disclosed herein are a composition for dyeing keratinous fibers, for example, human keratinous fibers such as hair, comprising at least one oxidation base chosen from diamino-N,N-dihydropyrazolone derivatives and the addition salts thereof and a method using the composition. Also disclosed herein are amino-N,N-dihydropyrazolone derivatives and diamino-N,N-dihydropyrazolone derivatives and the addition salts thereof, as well as methods of preparing these compounds.

It is known to dye keratinous fibers, for example, human keratinous fibers such as hair, with dyeing compositions containing oxidation dye precursors, such as ortho- and para-phenylenediamines, ortho- and para-aminophenols, and heterocyclic compounds such as diaminopyrazole derivatives, pyrazolo[1,5-a]pyrimidine derivatives, pyrimidine derivatives, pyridine derivatives, 5,6-dihydroxyindole derivatives, and 5,6-dihydroxyindoline derivatives, all of which are generally called oxidation bases. Oxidation dye precursors or oxidation bases are colorless or weakly colored compounds which, when combined with oxidizing products, can give rise, through a process of oxidative condensation, to colored or coloring compounds.

It is also known that it is possible to vary the shades obtained with these oxidation bases by combining them with couplers or color modifiers, wherein the couplers or color modifiers are chosen, for example, from meta-phenylenediamines, meta-aminophenols, meta-hydroxyphenols and certain heterocyclic compounds such as pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules used in oxidation bases and couplers allows a rich pallet of colors to be obtained.

The so-called "permanent" color obtained using these oxidation dyes should satisfy a number of requirements. Thus, it should be without drawbacks from the toxicological point of view, it should make it possible to obtain shades in the desired intensity and exhibit good resistance towards external agents such as light, adverse weather conditions, washing, permanent waving, perspiration, and rubbing.

The dyes should also make it possible to cover grey hair, and should be as unselective as possible, i.e., making it possible to obtain the smallest possible differences in color right along the same keratinous fiber, which may indeed be differently sensitized (i.e., damaged) between its tip and its root. The dyes should also have good chemical stability in their formulations and have a good toxicological profile.

The use of an oxidation base such as para-phenylenediamine or para-aminophenol derivatives makes it possible to obtain a fairly broad range of colors having a basic pH, but without, however, achieving shades of good chromaticity while at the same time conferring on hair excellent properties chosen from color intensity, shade variety, color uniformity and resistance to external agents.

The use of these oxidation bases having a neutral pH may furthermore be ineffective for obtaining a range of varied shades, such as for obtaining warm shades.

It has already been proposed in patent DE 3843892 to use certain diaminopyrazole derivatives, in particular for red to coppery red shades. However, this proposal does not make it possible to obtain good properties of chromaticity and of resistance to external agents such as washing and light. Furthermore, the breadth of the range of shades is limited.

Now, the present inventors have discovered, completely by surprise, that novel diamino-N,N-dihydropyrazolone compounds of formula (I) are suitable for use as oxidation dye precursors and make it possible to obtain a color with varied shades, which can be at least one of intense, chromatic, aesthetic, not very selective and can be quite resistant to the various attacks to which the hair may be subjected, such as shampoos, light, sweat and permanent waving.

The present inventors have also discovered, surprisingly, that the colors obtained at neutral pH using such compounds can be intense.

Therefore, disclosed herein is a composition for dyeing keratinous fibers comprising, in an appropriate dyeing medium, at least one oxidation base chosen from diamino-N,N-dihydropyrazolone derivatives of formula (I) and the addition salts and solvates thereof:

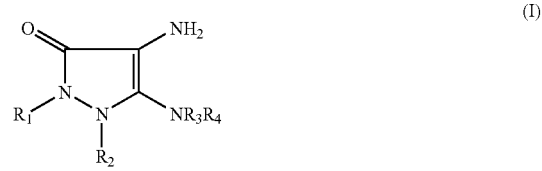

(I)

wherein:

$R_1$, $R_2$, $R_3$ and $R_4$, which are identical or different, are each chosen from:

linear and branched $C_1$-$C_6$ alkyl radicals optionally substituted with at least one radical chosen from a radical $OR_5$, a radical $NR_6R_7$, a carboxyl radical, a sulphonic radical, a carboxamido radical $CONR_6R_7$, a sulphonamido radical $SO_2NR_6R_7$, heteroaryl radicals, and aryl radicals optionally substituted with at least one radical chosen from ($C_1$-$C_4$)alkyl, hydroxyl, $C_1$-$C_2$ alkoxy, amino, and (di)alkyl($C_1$-$C_2$)amino radicals;

aryl radicals optionally substituted with at least one radical chosen from ($C_1$-$C_4$)alkyl, hydroxyl, $C_1$-$C_2$ alkoxy, amino, and (di)alkyl($C_1$-$C_2$)amino radicals; and 5- and, 6-membered heteroaryl radicals optionally substituted with at least one radical chosen from ($C_1$-$C_4$)alkyl and ($C_1$-$C_2$)alkoxy radicals;

$R_3$ and $R_4$ may also be a hydrogen atom;

$R_5$, $R_6$ and $R_7$, which are identical or different, are each chosen from a hydrogen atom; linear and branched $C_1$-$C_4$ alkyl radicals optionally substituted with at least one radical chosen from a hydroxyl radical, $C_1$-$C_2$ alkoxy radicals, carboxamido radicals $CONR_8R_9$, sulphonyl radicals $SO_2R_8$, and aryl radicals optionally substituted with at least one radical chosen from ($C_1$-$C_4$)alkyl, hydroxyl, $C_1$-$C_2$ alkoxy, amino, and (di)alkyl($C_1$-$C_2$)amino radicals; and aryl radicals optionally substituted with at least one radical chosen from ($C_1$-$C_4$) alkyl, hydroxyl, $C_1$-$C_2$ alkoxy, amino, and (di)alkyl($C_1$-$C_2$) amino radicals;

$R_6$ and $R_7$, which are identical or different, may also be chosen from carboxamido radicals $CONR_8R_9$ and sulphonyl radicals $SO_2R_8$;

$R_8$ and $R_9$, which are identical or different, are each chosen from a hydrogen atom; linear and branched $C_1$-$C_4$ alkyl radicals optionally substituted with at least one radical chosen from hydroxyl and $C_1$-$C_2$ alkoxy radicals;

$R_1$ and $R_2$, as well as $R_3$ and $R_4$, on the other hand, may, respectively, form, with the nitrogen atoms to which they are attached, a heterocycle chosen from saturated and unsaturated 5- to 7-membered heterocycles optionally substituted with at least one entity chosen from halogen atoms, and amino, (di)alkyl($C_1$-$C_4$)amino, hydroxyl, carboxyl, carboxamido and ($C_1$-$C_2$)alkoxy radicals, and $C_1$-$C_4$ alkyl radicals optionally substituted with at least one radical chosen from hydroxyl, amino, (di)alkylamino, alkoxy, carboxyl and sulphonyl radicals;

$R_3$ and $R_4$ may also form, together with the nitrogen atom to which they are attached, a heterocycle chosen from 5- and 7-membered heterocycles whose carbon atoms may be replaced with at least one optionally substituted atom chosen from optionally substituted oxygen and nitrogen atoms.

The present disclosure makes it possible, for example, to obtain a color on keratinous fibers which is fast and resistant to light and to washing.

Further disclosed herein is a method for dyeing keratinous fibers using the inventive composition, and the use of this composition for dyeing keratinous fibers.

Even further disclosed herein are novel amino-N,N-dihydropyrazolone derivatives of formula (I') and diamino-N,N-dihydropyrazolone derivatives of formula (I"), and the addition salts thereof, as well as novel methods of preparing these compounds.

As indicated above, the composition as disclosed herein comprises at least one oxidation base chosen from diamino-N,N-dihydropyrazolone derivatives of formula (I) and the addition salts and solvates thereof.

In one embodiment, in formula (I), the radicals $R_1$ and $R_2$, which are identical or different, are chosen from $C_1$-$C_4$ alkyl radicals optionally substituted with at least one radical chosen from hydroxyl, ($C_1$-$C_2$)alkoxy, amino, and (di)alkyl($C_1$-$C_2$)amino radicals; and a phenyl radical.

In another embodiment, the radicals $R_1$ and $R_2$, which are identical or different, are chosen from methyl, ethyl, 2-hydroxyethyl, 3-hydroxypropyl, 2-hydroxypropyl and phenyl radicals.

According to another embodiment, the radicals $R_1$ and $R_2$ form, together with the nitrogen atoms to which they are attached, a saturated or unsaturated, optionally substituted, 5- or 6-membered ring.

For example, the radicals $R_1$ and $R_2$ form, together with the nitrogen atoms to which they are attached, a pyrazolidine or pyridazolidine ring optionally substituted with at least one radical chosen from $C_1$-$C_4$ alkyl, hydroxyl, ($C_1$-$C_2$)alkoxy, carboxyl, carboxamido, amino, and (di)alkyl($C_1$-$C_2$)amino radicals.

In another embodiment, the radicals $R_1$ and $R_2$ form, together with the nitrogen atoms to which they are attached, a pyrazolidine or pyridazolidine ring.

The radicals $R_3$ and $R_4$, which are identical or different, are, for example, chosen from a hydrogen atom; linear and branched $C_1$-$C_4$ alkyl radicals optionally substituted with at least one radical chosen from hydroxyl, ($C_1$-$C_2$)alkoxy, amino, and (di)alkyl($C_1$-$C_2$)amino radicals; a phenyl radical optionally substituted with at least one radical chosen from hydroxyl, amino and ($C_1$-$C_2$)alkoxy radicals.

In one embodiment, the radicals $R_3$ and $R_4$, which are identical or different, are chosen from a hydrogen atom, and methyl, ethyl, isopropyl, 2-hydroxyethyl, 3-hydroxypropyl, 2-hydroxypropyl and 2-carboxyethyl radicals. According to one embodiment, the radicals $R_3$ and $R_4$ are each a hydrogen atom.

According to another embodiment, the radicals $R_3$ and $R_4$ form, together with the nitrogen atom to which they are attached, a 5- or 7-membered ring chosen from pyrrolidine, piperidine, homopiperidine, piperazine and homopiperazine heterocycles; wherein it is possible for the rings to be substituted with at least one radical chosen from hydroxyl, amino, (di)alkyl($C_1$-$C_2$)amino, carboxyl and carboxamido radicals, and $C_1$-$C_4$ alkyl radicals optionally substituted with at least one radical chosen from hydroxyl, amino, and $C_1$-$C_2$ (di) alkylamino radicals.

In another embodiment, the radicals $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethyl-piperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamido-homopiperidine, homopiperazine, N-methylhomopiperazine, and N-(2-hydroxyethyl)homopiperazine.

In one embodiment, the radicals $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-β-hydroxyethylhomopiperazine.

In accordance with one embodiment, the radicals $R_3$ and $R_4$ form, together with the nitrogen atom to which they are attached, a 5-membered ring chosen, for example, from pyrrolidine, 3-hydroxypyrrolidine, 3-aminopyrrolidine, and 3-dimethylaminopyrrolidine.

The compounds of formula (I) may be optionally salified with at least one acid chosen from strong inorganic acids such as HCl, HBr, HI, $H_2SO_4$, $H_3PO_4$, and organic acids such as acetic, lactic, tartaric, citric and succinic, benzenesulphonic, para-toluenesulphonic, formic and methanesulphonic acids.

The compounds of formula (I) may also be in the form of solvates, for example, a hydrate or a solvate of a linear or branched alcohol such as ethanol and isopropanol.

Examples of the compounds of formula (I) and the addition salts thereof include:
4,5-diamino-1,2-dimethyl-1,2-dihydropyrazol-3-one,
4-amino-5-methylamino-1,2-dimethyl-1,2-dihydropyrazol-3-one, 4-amino-5-dimethylamino-1,2-dimethyl-1,2-dihydropyrazol-3-one,
4-amino-5-(2-hydroxyethyl)amino-1,2-dimethyl-1,2-dihydropyrazol-3-one,
4-amino-5-(pyrrolidin-1-yl)-1,2-dimethyl-1,2-dihydropyrazol-3-one,
4-amino-5-(piperidin-1-yl)-1,2-dimethyl-1,2-dihydropyrazol-3-one,
4,5-diamino-1,2-di(2-hydroxyethyl)-1,2-dihydropyrazol-3-one,
4-amino-5-methylamino-1,2-di(2-hydroxyethyl)-1,2-dihydropyrazol-3-one,
4-amino-5-dimethylamino-1,2-di(2-hydroxyethyl)-1,2-dihydropyrazol-3-one,
4-amino-5-(2-hydroxyethyl)amino-1,2-di(2-hydroxyethyl)-1,2-dihydropyrazol-3-one,
4-amino-5-(pyrrolidin-1-yl)-1,2-di(2-hydroxyethyl)-1,2-dihydropyrazol-3-one,
4-amino-5-(piperidin-1-yl)-1,2-di(2-hydroxyethyl)-1,2-dihydropyrazol-3-one,
4,5-diamino-1,2-diethyl-1,2-dihydropyrazol-3-one,
4,5-diamino-1,2-phenyl-1,2-dihydropyrazol-3-one,
4,5-diamino-1-ethyl-2-methyl-1,2-dihydropyrazol-3-one,
4,5-diamino-2-ethyl-1-methyl-1,2-dihydropyrazol-3-one,
4,5-diamino-1-phenyl-2-methyl-1,2-dihydropyrazol-3-one,
4,5-diamino-1-(2-hydroxyethyl)-2-methyl-1,2-dihydropyrazol-3-one,
4,5-diamino-2-(2-hydroxyethyl)-1-methyl-1,2-dihydropyrazol-3-one,
2,3-diamino-6,7-dihydro-1H,5H-pyrazolo[1,2-a]pyrazol-1-one,
2-amino-3-methylamino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(2-hydroxyethyl)amino-6,7-dihydro-1H,5H-pyrazolo[1,2-a]pyrazol-1-one,
2-amino-3-(2-hydroxypropyl)amino-6,7-dihydro-1H,5H-pyrazolo[1,2-a]pyrazol-1-one,
2-amino-3-bis(2-hydroxyethyl)amino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
2-amino-3-(3-hydroxypyrrolidin-1-yl)-6,7-dihydro-1H,5H-pyrazolo[1,2-a]pyrazol-1-one,
2-amino-3-(piperidin-1-yl)-6,7-dihydro-1H,5H-pyrazolo[1,2-a]pyrazol-1-one,
2,3-diamino-6-hydroxy-6,7-dihydro-1H,5H-pyrazolo[1,2-a]pyrazol-1-one,
2,3-diamino-6-methyl-6,7-dihydro-1H,5H-pyrazolo[1,2-a]pyrazol-1-one,
2,3-diamino-6-dimethyl-6,7-dihydro-1H,5H-pyrazolo[1,2-a]pyrazol-1-one,
2,3-diamino-5,6,7,8-tetrahydro-1H,6H-pyridazino[1,2-a]pyrazol-1-one,
2,3-diamino-5,8-dihydro-1H,6H-pyridazino[1,2-a]pyrazol-1-one,
4-amino-5-dimethylamino-1,2-diethyl-1,2-dihydropyrazol-3-one,
4-amino-1,2-diethyl-5-ethylamino-1,2-dihydropyrazol-3-one,
4-amino-1,2-diethyl-5-isopropylamino-1,2-dihydropyrazol-3-one,
4-amino-1,2-diethyl-5-(2-hydroxyethylamino)-1,2-dihydropyrazol-3-one,
4-amino-5-(2-dimethylaminoethylamino)-1,2-diethyl-1,2-dihydropyrazol-3-one,
4-amino-5-[bis(2-hydroxyethyl)amino]-1,2-diethyl-1,2-dihydropyrazol-3-one,
4-amino-1,2-diethyl-5-(3-imidazol-1-ylpropylamino)-1,2-dihydropyrazol-3-one,
4-amino-5-dimethylamino-1,2-diethyl-1,2-dihydropyrazol-3-one,
4-amino-1,2-diethyl-5-ethylamino-1,2-dihydropyrazol-3-one,
4-amino-1,2-diethyl-5-isopropylamino-1,2-dihydropyrazol-3-one,
4-amino-1,2-diethyl-5-(2-hydroxyethylamino)-1,2-dihydropyrazol-3-one,
4-amino-5-(2-dimethylaminoethylamino)-1,2-diethyl-1,2-dihydropyrazol-3-one,
4-amino-5-[bis(2-hydroxyethyl)amino]-1,2-diethyl-1,2-dihydropyrazol-3-one,
4-amino-1,2-diethyl-5-(3-imidazol-1-ylpropylamino)-1,2-dihydropyrazol-3-one,
4-amino-1,2-diethyl-5-(3-hydroxypyrrolidin-1-yl)-1,2-dihydropyrazol-3-one,
4-amino-1,2-diethyl-5-pyrrolidin-1-yl-1,2-dihydropyrazol-3-one,
4-amino-5-(3-dimethylaminopyrrolidin-1-yl)-1,2-diethyl-1,2-dihydropyrazol-3-one,
4-amino-1,2-diethyl-5-(4-methylpiperazin-1-yl)pyrazolidin-3-one, and
2,3-diamino-6-hydroxy-6,7-dihydro-5H-pyrazolo[1,2-a]pyrazol-1-one, some of which are presented below to illustrate their names by chemical structures:

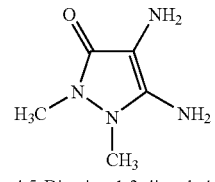
4,5-Diamino-1,2-dimethyl-1,2-dihydropyrazol-3-one

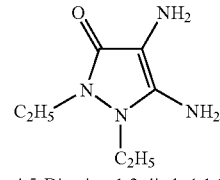
4,5-Diamino-1,2-diethyl-1,2-dihydropyrazol-3-one

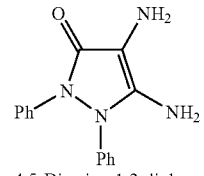
4,5-Diamino-1,2-diphenyl-1,2-dihydropyrazol-3-one

-continued

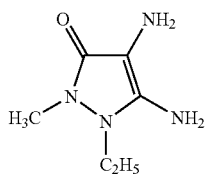

4,5-Diamino-1-ethyl-2-methyl-1,2-dihydropyrazol-3-one

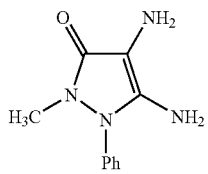

4,5-Diamino-1-phenyl-2-methyl-1,2-dihydropyrazol-3-one

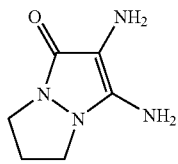

2,3-Diamino-6,7-dihydro-1H,5H-pyrazolo[1,2-a]pyrazol-1-one

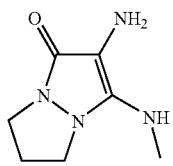

2-Amino-3-methylamino-6,7-dihydro-1H,5H-pyrazolo[1,2-a]pyrazol-1-one

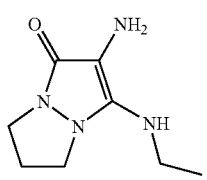

2-Amino-3-ethylamino-6,7-dihydro-1H,5H-pyrazolo[1,2-a]pyrazol-1-one

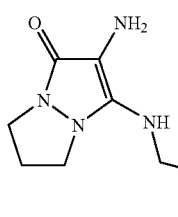

2-Amino-3-(2-hydroxyethyl)amino-6,7-dihydro-1H,5H-pyrazolo[1,2-a]pyrazol-1-one

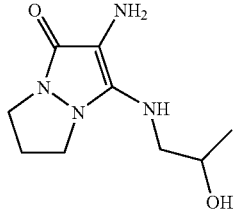

2-Amino-3-(2-hydroxypropyl)amino-6,7-dihydro-1H,5H-pyrazolo[1,2-a]pyrazol-1-one

-continued

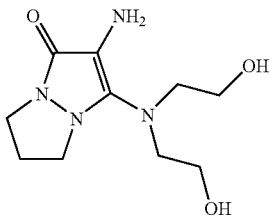

2-Amino-3-bis(2-hydroxyethyl)amino-6,7-dihydro-1H,5H-pyrazolo[1,2-a]pyrazol-1-one

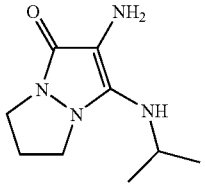

2-Amino-3-isopropylamino-6,7-dihydro-1H,5H-pyrazolo[1,2-a]pyrazol-1-one

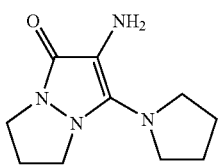

2-Amino-3-(pyrrolidin-1-yl)-6,7-dihydro-1H,5H-pyrazolo[1,2-a]pyrazol-1-one

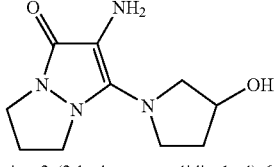

2-Amino-3-(3-hydroxypyrrolidin-1-yl)-6,7-dihydro-1H,5H-pyrazolo[1,2-a]pyrazol-1-one

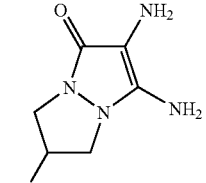

2,3-Diamino-6-hydroxy-6,7-dihydro-1H,5H-pyrazolo-[1,2-a]pyrazol-1-one

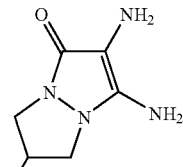

2,3-Diamino-6-methyl-6,7-dihydro-1H,5H-pyrazolo[1,2-a]pyrazol-1-one

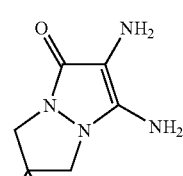

2,3-Diamino-6-dimethyl-6,7-dihydro-1H,5H-pyrazolo[1,2-a]pyrazol-1-one

-continued

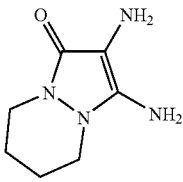
2,3-Diamino-5,6,7,8-tetrahydro-1H,6H-pyridazino[1,2-a]pyrazol-1-one

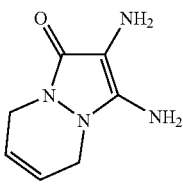
2,3-Diamino-5,8-dihydro-1H,6H-pyridazino[1,2-a]pyrazol-1-one

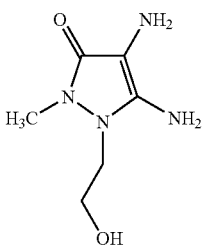
4,5-Diamino-1-(2-hydroxyethyl)-2-methyl-1,2-dihydropyrazol-3-one

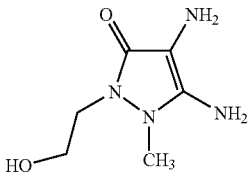
4,5-Diamino-2-(2-hydroxyethyl)-1-methyl-1,2-dihydropyrazol-3-one

Among these compounds, examples of the diamino-N,N-dihydropyrazolone derivatives of formula (I) and their addition salts include:
2,3-diamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
4,5-diamino-1,2-dimethyl-1,2-dihydropyrazol-3-one,
4,5-diamino-1,2-diethyl-1,2-dihydropyrazol-3-one,
4,5-diamino-1,2-di(2-hydroxyethyl)-1,2-dihydropyrazol-3-one,
2-amino-3-(2-hydroxyethyl)amino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one, and
2,3-diamino-5,6,7,8-tetrahydro-1H,6H-pyridazino[1,2-a]pyrazol-1-one.

The at least one oxidation base as disclosed herein is generally present in an amount ranging from 0.001 to 10%, such as from 0.005 to 6%, by weight relative to the total weight of the dyeing composition.

The dyeing composition as disclosed herein may comprise at least one coupler chosen from the couplers conventionally used for dyeing keratinous fibers. Among these couplers, mention may be made, for example, of meta-phenylenediamines, meta-aminophenols, meta-diphenols, naphthalene couplers, heterocyclic couplers and their addition salts.

By way of example, the at least one coupler may be chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and the acid addition salts thereof.

In the composition as disclosed herein, the at least one coupler is generally present in an amount ranging from 0.001 to 10%, such as from 0.005 to 6%, by weight relative to the total weight of the dyeing composition.

The composition as disclosed herein may further comprise at least one additional oxidation base chosen from oxidation bases conventionally used in oxidation dyeing other than those described above. By way of example, the at least one additional oxidation base is chosen from para-phenylenediamines, bisphenylalkylenediamines, para-aminophenols, bis-para-aminophenols, ortho-aminophenols, ortho-phenylenediamines, and heterocyclic bases different from the compounds of formula (I) as defined above and their addition salts.

Among the para-phenylenediamines, there may be mentioned, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(D-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine and the acid addition salts thereof.

Among the para-phenylenediamines mentioned above, examples include para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Among the bisphenylalkylenediamines, there may be mentioned, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Among the para-aminophenols, there may be mentioned, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Among the ortho-aminophenols, there may be mentioned, by way of example, 2-aminophenol, 2-amino-5-methylphenol, 2-amino-6-methylphenol, 5-acetamido-2-aminophenol, and the acid addition salts thereof.

Among the heterocyclic bases, there may be mentioned, by way of example, pyridine derivatives, pyrimidine derivatives and pyrazole derivatives.

Among the pyridine derivatives, there may be mentioned the compounds described, for example, in patents GB 1,026,978 and GB 1,153,196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Other pyridine oxidation bases useful in the present disclosure include, for example, the oxidation bases 3-aminopyrazolo[1,5-a]pyridines and their addition salts which are described, for example, in patent application FR 2801308. By way of example, there may be mentioned pyrazolo[1,5-a]pyridin-3-ylamine; 2-acetylaminopyrazolo[1,5-a]pyridin-3-ylamine; 2-morpholin-4-ylpyrazolo[1,5-a]pyridin-3-ylamine; 3-aminopyrazolo[1,5-a]pyridine-2-carboxylic acid; 2-methoxypyrazolo[1,5-a]pyridin-3-ylamino; (3-aminopyrazolo[1,5-a]pyridin-7-yl)methanol; 2-(3-aminopyrazolo[1,5-a]pyridin-5-yl)methanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridin-3-ylamine; pyrazolo[1,5-a]pyridine-3,5-diamine; 5-morpholin-4-ylpyrazolo[1,5-a]pyridin-3-ylamine; 2-[(3-aminopyrazol[1,5-a]pyridin-5-yl)(2-hydroxyethyl)amino]ethanol; 2-[(3-aminopyrazolo[1,5-a]pyridin-7-yl)(2-hydroxyethyl)amino]ethanol, 3-aminopyrazolo[1,5-a]pyridin-5-ol; 3-aminopyrazolo[1,5-a]pyridin-5-ol, 3-aminopyrazolo[1,5-a]pyridin-6-ol; 3-aminopyrazolo[1,5-a]pyridin-7-ol; and the acid and base addition salts thereof.

Among the pyrimidine derivatives, there may be mentioned the compounds described, for example, in patents DE 2,359,399; JP 88-169,571; JP 05-63124; and EP 0770375 and patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in patent application FR-A-2,750,048 and among which there may be mentioned, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine and their acid addition salts and their tautomeric forms, when a tautomeric equilibrium exists.

Among the pyrazole derivatives, there may be mentioned the compounds described in, for example, patents DE 3,843,892, DE 4,133,957 and patent applications WO 94/08969, WO 94/08970, FR-A-2,733,749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

The at least one additional oxidation base in the composition as disclosed herein is generally present in an amount ranging from 0.001 to 10%, such as from 0.005 to 6%, by weight relative to the total weight of the dyeing composition.

In general, the addition salts of the oxidation bases and couplers which can be used in the context of the present disclosure are, for example, chosen from the addition salts with an acid such as hydrochlorides, hydrobromides, sulphates, citrates, succinates, tartrates, lactates, tosylates, benzenesulphonates, phosphates and acetates and the addition salts with a base such as sodium hydroxide, potassium hydroxide, ammonium hydroxide, amines and alkanolamines.

The dyeing composition as disclosed herein may, in addition, comprise at least one direct dye chosen, for example, from nitro dyes of the benzene series, azo direct dyes and methine direct dyes. These direct dyes may be of a nonionic, anionic or cationic nature.

The medium appropriate for dyeing, also called the dye carrier, is a cosmetic medium generally comprising water or a mixture of water and at least one organic solvent for solubilizing the compounds which might not be sufficiently soluble in water. The at least one organic solvent may be chosen, for example, from lower $C_1$-$C_4$ alkanols, such as ethanol and isopropanol; polyols and polyol ethers such as 2-butoxyethanol, propylene glycol, propylene glycol monomethyl ether, diethylene glycol monoethyl ether and monomethyl ether, and aromatic alcohols such as benzyl alcohol and phenoxyethanol, and mixtures thereof.

The at least one organic solvent is, for example, present in an amount ranging from 1 to 40%, such as from 5 to 30%, by weight relative to the total weight of the dyeing composition.

The dyeing composition as disclosed herein may also comprise at least one adjuvant chosen from various adjuvants conventionally used in hair dyeing compositions, such as anionic, cationic, nonionic, amphoteric and zwitterionic surfactants and mixtures thereof, anionic, cationic, nonionic, amphoteric and zwitterionic polymers and mixtures thereof, inorganic and organic thickeners, such as the associative thickeners, anionic, cationic, nonionic and amphoteric polymers, antioxidants, penetrating agents, sequestrants, perfumes, buffers, dispersing agents, conditioning agents such as modified and unmodified, volatile and nonvolatile silicones, film-forming agents, ceramides, preservatives, and opacifying agents.

The at least one adjuvant is generally present in an amount ranging from 0.01 to 20% by weight relative to the total weight of the dyeing composition.

Of course, persons skilled in the art will be careful to choose this or these optional additional compounds such that the advantageous properties intrinsically attached to the oxidation dyeing composition as disclosed herein are not, or not substantially, impaired by the addition(s) envisaged.

The pH of the dyeing composition as disclosed herein generally ranges from 3 to 12, such as from 5 to 11. It may be adjusted to the desired value by at least one agent chosen from acidifying and alkalinizing agents customarily used in dyeing keratinous fibers or with the aid of conventional buffering systems.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid, and sulphonic acids.

Among the alkalinizing agents, there may be mentioned, by way of example, ammonium hydroxide, alkali metal carbonates, alkanolamines such as mono-, di- and triethanolamines and the derivatives thereof, sodium and potassium hydroxides and the compounds of the following formula (II):

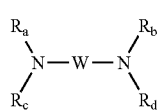

(II)

wherein W is a propylene residue optionally substituted with at least one radical chosen from hydroxyl and $C_1$-$C_4$ alkyl radicals; $R_a$, $R_b$, $R_c$ and $R_d$, which may be identical or different, are each chosen from a hydrogen atom, $C_1$-$C_4$ alkyl radicals and $C_1$-$C_4$ hydroxyalkyl radicals.

The dyeing composition as disclosed herein may be provided in various forms, such as in the form of liquids, creams and gels, or in any other appropriate form for dyeing keratinous fibers, such as human hair.

The method disclosed herein comprises applying the composition according to the present disclosure, as defined above, to the keratinous fibers, in which the color is developed using at least one oxidizing agent. The color may be developed at acidic, neutral or alkaline pH and the oxidizing agent may be added to the composition as disclosed herein just at the time of use or it can be used from an oxidizing composition containing it, applied simultaneously or sequentially with the composition as disclosed herein.

In one embodiment, the composition as disclosed herein is mixed, such as at the time of use, with a composition comprising, in a medium appropriate for dyeing, at least one oxidizing agent, wherein the at least one oxidizing agent is present in a sufficient quantity to develop a color. The mixture obtained is then applied to the keratinous fibers. After an exposure time ranging from 3 to 50 minutes, such as from 5 to 30 minutes, the keratinous fibers are rinsed, washed with shampoo, rinsed again and then dried.

The at least one oxidizing agent is chosen from those conventionally used for the oxidation dyeing of keratinous fibers, for example, hydrogen peroxide, urea peroxide, alkali metal bromates, persalts such as perborates and persulphates, peracids and the oxidase enzymes, among which there may be mentioned peroxidases, oxidoreductases with 2 electrons such as uricases and oxygenases with 4 electrons such as laccases. In one embodiment, hydrogen peroxide is used.

The oxidizing composition may also comprise at least one adjuvant chosen from various adjuvants conventionally used in hair dyeing compositions and as defined above.

The pH of the oxidizing composition containing the oxidizing agent is such that, after mixing with the dyeing composition, the pH of the resulting composition applied to keratinous fibers ranges, for example, from 3 to 12, such as from 5 to 11. It may be adjusted to the desired value by at least one agent chosen from acidifying and alkalinizing agents customarily used for dyeing keratinous fibers and as defined above.

The ready-to-use composition which is finally applied to the keratinous fibers may be provided in various forms, such as in the form of liquids, creams and gels, or in any other form appropriate for dyeing keratinous fibers, such as human hair.

Further disclosed herein is a multicompartment device or dyeing "kit" in which a first compartment comprises the dyeing composition as defined above and a second compartment comprises an oxidizing composition. This device may be equipped with tools which make it possible to deliver the desired mixture to the hair, such as the devices described in patent FR-2 586 913.

Using this device, it is possible to dye keratinous fibers using a method, which comprises mixing the dyeing composition comprising at least one oxidation base of formula (I) with at least one oxidizing agent, and applying the mixture obtained to the keratinous fibers for a time sufficient to develop the desired color.

Further disclosed herein is the use, for the oxidation dyeing of keratinous fibers, for example, human keratinous fibers such as hair, of the diamino-N,N-dihydropyrazolone derivative of formula (I) or of one of its addition salts as defined above.

Even further disclosed herein are amino-N,N-dihydropyrazolone derivatives of the following formula (I'), and their addition salts:

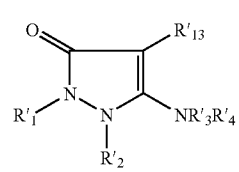

(I')

wherein:
$R'_1$, $R'_2$, $R'_3$ and $R'_4$ respectively have the same meanings as $R_1$, $R_2$, $R_3$ and $R_4$, and $R'_{13}$ is chosen from nitro, nitroso and arylazo Ar—N=N— groups wherein the aryl radical Ar is optionally substituted with at least one entity chosen from C$_1$-C$_4$ alkyl, amino, (di)alkyl(C$_1$-C$_4$)amino, C$_1$-C$_2$ alkoxy, sulphonic, and carboxyl radicals and halogen atoms, provided that R'$_1$ and R'$_2$ are not simultaneously a methyl radical when R'$_3$ and R'$_4$ are each a hydrogen atom and R'$_{13}$ is not a group Ar—N=N— when R'$_3$ and R'$_4$ simultaneously are each a hydrogen atom.

All that has been stated above regarding the definitions of the radicals R$_1$, R$_2$, R$_3$ and R$_4$ applies to R'$_1$, R'$_2$, R'$_3$ and R'$_4$ and will not be repeated in this part of the text.

Further disclosed herein are diamino-N,N-dihydropyrazolone derivatives of the following formula (I"), and their addition salts:

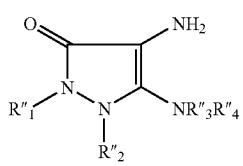
(I")

wherein R"$_1$, R"$_2$, R"$_3$ and R"$_4$ have the same meanings as those stated above for R'$_1$, R'$_2$, R'$_3$ and R'$_4$.

Here again, all that has been stated above regarding the definitions of the radicals R'$_1$, R'$_2$, R'$_3$ and R'$_4$ applies to R"$_1$, R"$_2$, R"$_3$ and R"$_4$ and will not be repeated in this part of the text.

The amino-N,N-dihydropyrazolone derivatives and diamino-N,N-dihydropyrazolone derivatives as disclosed herein, wherein the radicals R'$_3$ and R'$_4$, as well as R"$_3$ and R"$_4$, respectively, are a hydrogen atom, may be obtained from intermediates and routes of synthesis described in the literature such as: *J. Het. Chem.*, 2001, 38(3), 613-616, *Helvetica Chimica Acta*, 1950, 33, 1183-1194, *J. Org. Chem.*, 23, 2029 (1958), *J. Am. Chem. Soc.*, 73, 3240 (1951), *J. Am. Chem. Soc.*, 84, 590 (1962), *Justus Liebig Ann. Chem.*, 686, 134 (1965), *Tetrahedron Lett.*, 31, 2859-2862 (1973), and U.S. Pat. Nos. 4,128,425 and 2,841,584 and the references cited therein.

According to these references, the compounds of formula (I) having R$_3$ and R$_4$ equal to hydrogen atoms may be obtained from the route of synthesis represented in scheme A below:

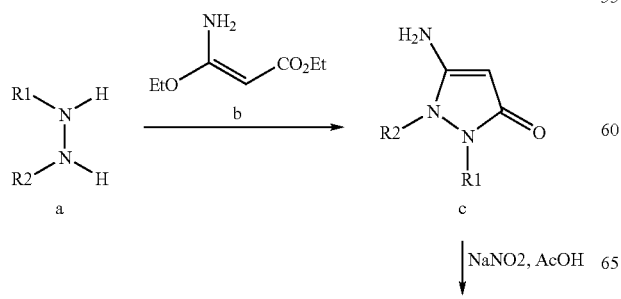

Scheme A

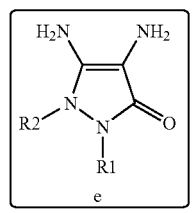
e

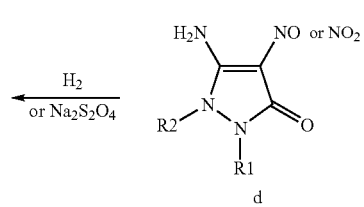
d

The compounds as disclosed herein wherein R$_1$ and R$_2$ simultaneously are each a methyl group and R$_3$ and R$_4$ simultaneously are each a hydrogen atom may be obtained based on the method described in *Justus Lieb. Ann. Chem.*, 686, 134 (1965) (scheme B):

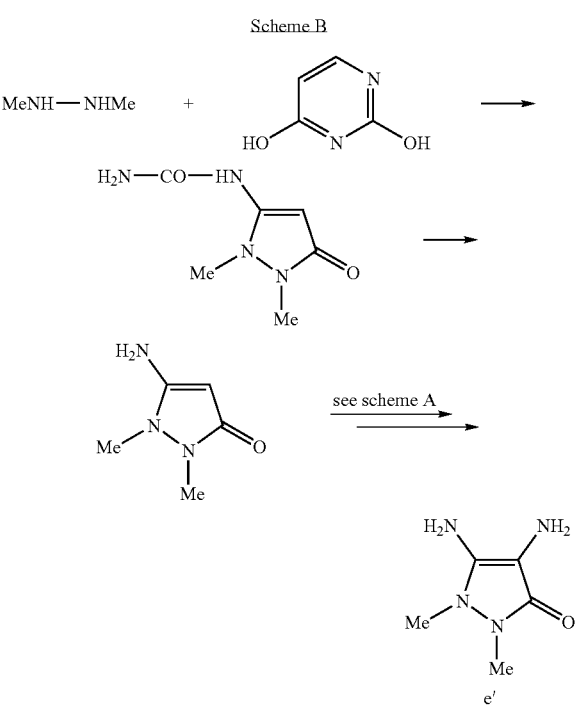

Scheme B

The compounds as disclosed herein wherein R$_1$ is a methyl group, R$_2$ is a phenyl radical, and R$_3$ and R$_4$ simultaneously are each a hydrogen atom may be obtained based on the method described in *J. Org. Chem.*, 23, 2029 (1958) and *J. Am. Chem. Soc.*, 73, 3240 (1951) (scheme C):

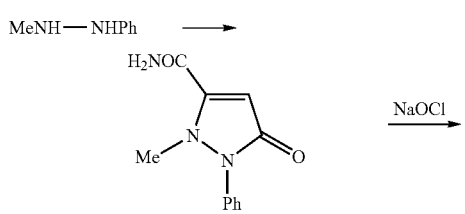

Scheme C

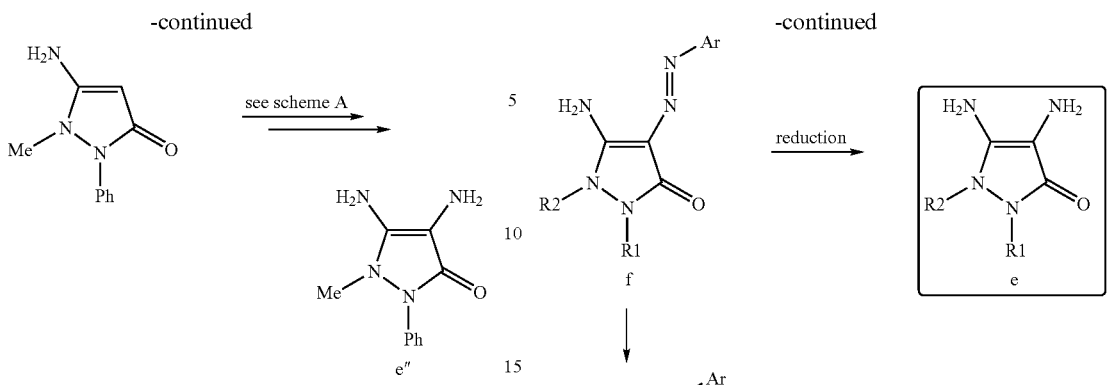

The compounds as disclosed herein wherein $R_1$ and $R_2$ form together with the nitrogen atoms to which they are attached a 5-membered ring and $R_3$ and $R_4$ simultaneously are each a hydrogen atom may be obtained based on the method described in *J. Het. Chem.*, 2001, 38(3), 613-616 (scheme D):

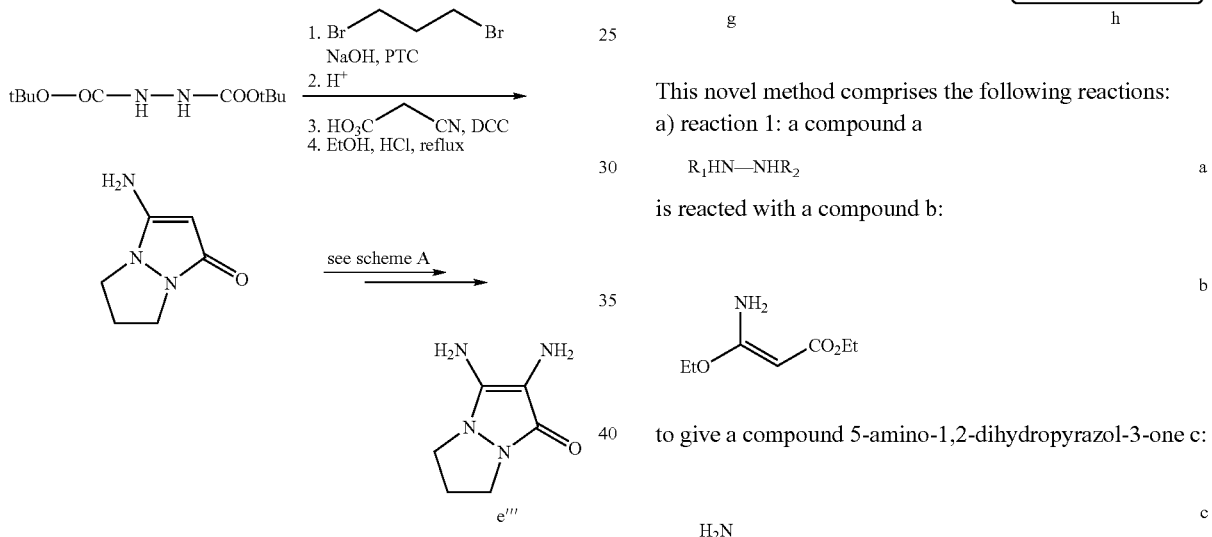

According to a novel method disclosed herein, the compounds of formula (I) may be obtained according to the synthesis illustrated in scheme E:

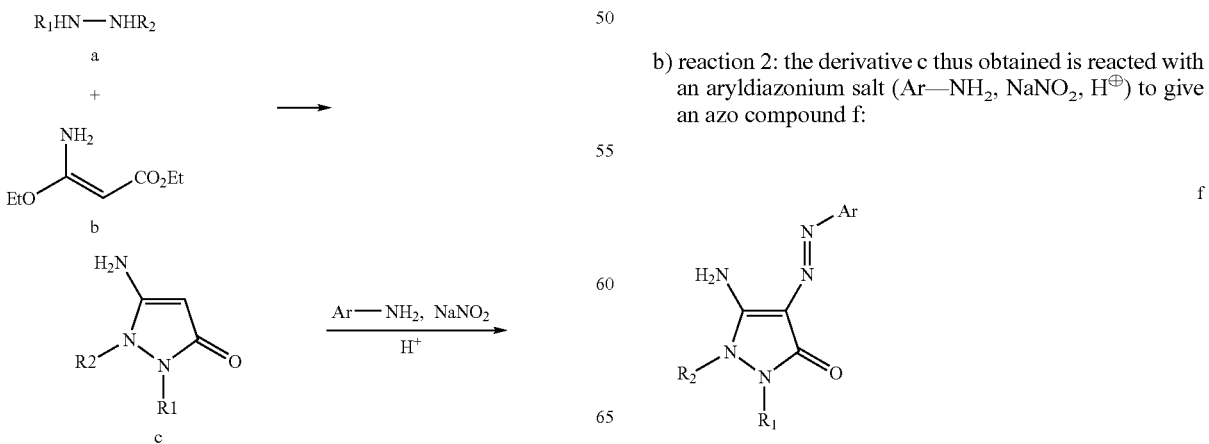

This novel method comprises the following reactions:

a) reaction 1: a compound a $R_1HN—NHR_2$      a is reacted with a compound b:

b to give a compound 5-amino-1,2-dihydropyrazol-3-one c:

c b) reaction 2: the derivative c thus obtained is reacted with an aryldiazonium salt ($Ar—NH_2$, $NaNO_2$, $H^{\oplus}$) to give an azo compound f:

f c) reaction 3: functionalizing the primary amine group of the resulting azo compound f is optionally carried out in order to give the following compound g:

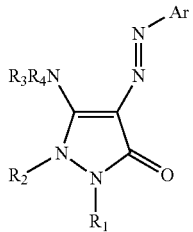

d) reaction 4: a reaction of reduction of the azo compound f or g is carried out in order to obtain an amine-containing compound e or h respectively:

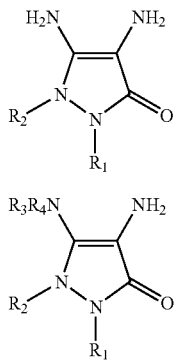

The optional reaction of functionalizing the primary amine group at the 5-position to a secondary and tertiary amine $NR_3R_4$ in order to give the compounds g, is carried out according to conventional methods of organic synthesis (alkyl halide, alkyl O-sulphonate, alkyl trialkylammonium, reductive amination, and the like, see for example *Advanced Organic Chemistry*, 3rd edition, 1985, J. March, Wiley Interscience).

The reduction of the azo group leads to compounds e and h in accordance with the present disclosure.

The reduction is carried out in a conventional manner, for example, by carrying out a hydrogenation reaction by heterogeneous catalysis in the presence of Pd/C, Pd(II)/C, Ni/Ra, and the like or alternatively by carrying out a reduction reaction with a metal, for example with zinc, iron, tin and the like (see *Advanced Organic Chemistry*, 3rd edition, J. March, 1985, Wiley Interscience and *Reduction in Organic Chemistry*, M. Hudlicky, 1983, Ellis Horwood Series Chemical Science).

According to a novel method disclosed herein, the 2,3-diamino-6,7-dihydro-1H,5H-pyrazolo[1,2-a]pyrazol-1-one and 2,3-diamino-5,6,7,8-tetrahydro-1H,6H-pyridazino[1,2-a]pyrazol-1-one derivatives in accordance with formula (I) are obtained according to the synthesis illustrated by scheme F:

Scheme F

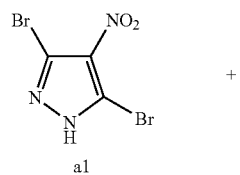

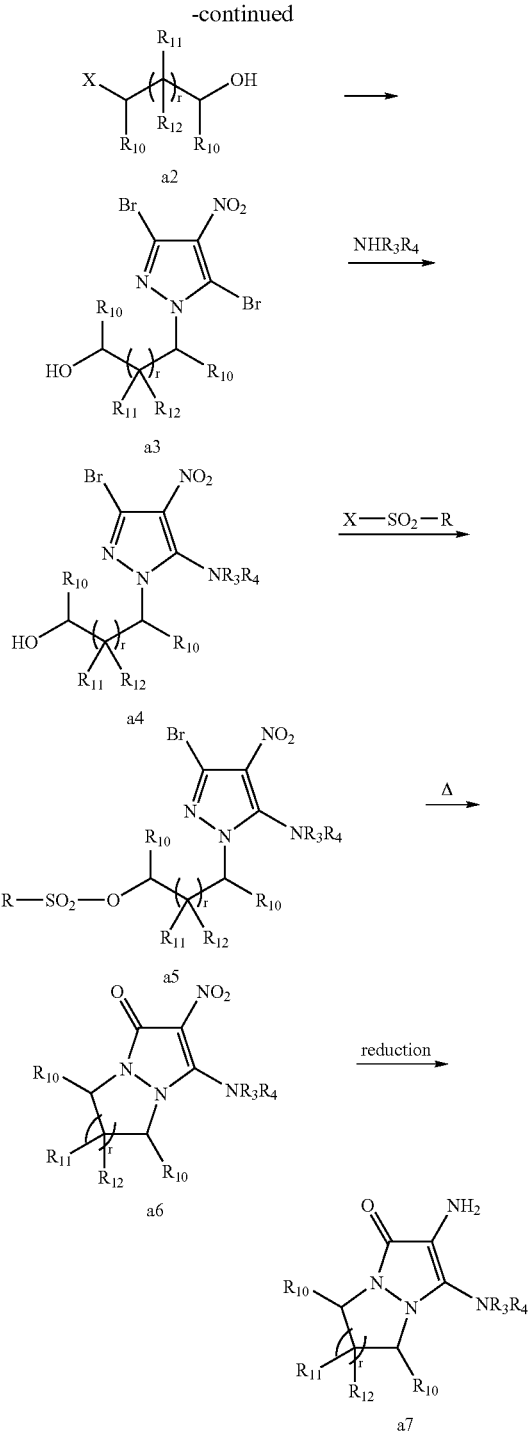

This novel method comprises the following reactions:

a) reaction 1: the following compound a1:

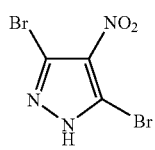

is reacted with a compound a2:

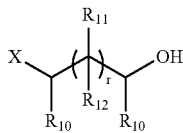

a2 to give a compound a3:

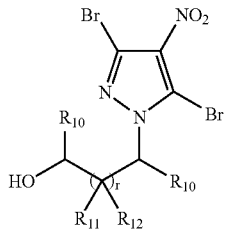

a3 wherein:

$R_{10}$ is chosen from a hydrogen atom, a carboxyl radical; a carboxamido radical; $C_1$-$C_4$ alkyl radicals optionally substituted with at least one radical chosen from hydroxyl, amino, (di)alkylamino, alkoxy, carboxyl and sulphonyl radicals;

$R_{11}$ and $R_{12}$, which may be identical or different, are each chosen from hydrogen and halogen atoms; an amino radical; (di)alkyl($C_1$-$C_4$)amino radicals; a hydroxyl radical; a carboxyl radical; a carboxamido radical; ($C_1$-$C_2$)alkoxy radicals; $C_1$-$C_4$ alkyl radicals optionally substituted with at least one radical chosen from hydroxyl, amino, (di)alkylamino, alkoxy, carboxyl and sulphonyl radicals;

X is chosen from halogen atoms and alkyl sulphonates;

r is an integer ranging from 1 to 3;

b) reaction 2: the compound a3 is reacted with an amine of formula $NHR_3R_4$ to give a compound a4:

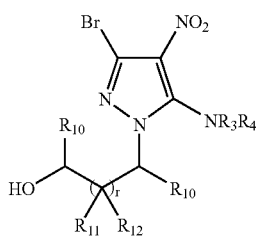

a4 c) reaction 3: the compound a4 is reacted with at least one compound chosen from alkylsulphonyl, arylsulphonyl and perfluoroalkylsulphonyl halides R—$O_2$S—X, (wherein R is chosen from alkyl, aryl and perfluoroalkyl radicals, and $X_1$ is chosen from halogen atoms), in a solvent having a boiling point ranging from 60° C. to 190° C. in order to give a compound a5:

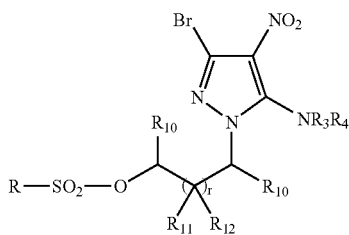

a5 d) reaction 4: the resulting compound a5 is then heated in a solvent having a boiling point ranging from 60° C. to 190° C. to give a compound a6:

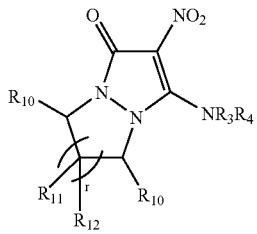

a6 e) reaction 5: the compound a6 obtained is reduced to give the compound a7 of formula below (III):

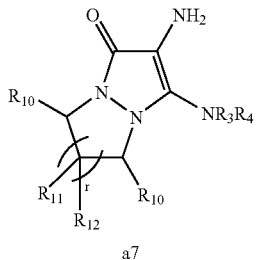

Formula (III)

a7

For example, according to this method, 3,5-dibromo-4-nitropyrazole a1, obtained according to the method described, for example, in document DE 4234885, reacts with the reagent a2, such as in a solvent having a boiling point ranging from 60° C. to 190° C. By way of example, there may be mentioned pentanol, dimethylformamide, and N-methylpyrrolidine. In one embodiment, the reduction is carried out in the presence of at least one base chosen from organic and inorganic bases, such as sodium carbonate, sodium hydroxide, sodium acetate and triethylamine. The temperature of the reaction medium is, for example, maintained at a range of from 60° C. to 160° C., such as from 80° C. to 120° C.

1-Hydroxyalkyl-3,5-dibromo-4-nitropyrazole a3 is, for example, isolated by precipitation or crystallization after adding ice to the reaction medium.

In reaction 2, the derivative a3 is reacted with an amine $NHR_3R_4$, for example, in a solvent having a boiling point ranging from 60° C. to 190° C. such as butanol, pentanol, and dimethylformamide. The temperature may range, for example, from 60° C. to 160° C., such as from 80° C. to 120° C. After consuming the reagents, the compound 5-amino-4-nitro-3-bromo-1-hydroxyalkylpyrazole a4 is isolated by precipitation or crystallization using water.

In accordance with reaction 3, the derivative a5 is obtained by reaction of the alcohol a4 and of a compound chosen from alkylsulphonyl, arylsulphonyl and perfluoroalkylsulphonyl halides. The reaction takes place, for example, in an aprotic solvent such as tetrahydrofuran and dioxane. In one embodiment, the reaction takes place at a temperature ranging from −20° C. to 60° C., such as from 0° C. to 25° C. Furthermore, this reaction takes place in the presence of at least one base chosen from organic and inorganic bases such as potassium carbonate, triethylamine, and N-methylmorpholine. After the disappearance of the reagents, compound a5 is isolated by precipitation or crystallization from water.

In reaction 4, the sulphonate a5 obtained at the end of reaction 3 is dissolved, or dispersed in a solvent having a boiling point ranging from 60° C. to 190° C., such as from 90° C. to 140° C. The temperature of the reaction medium is then brought to a temperature ranging from 90° C. to 140° C., such as from 105° C. to 125° C. until there is total consumption of the sulphonate a5. After returning to room temperature, the perhydropyrazolo[1,2-a]pyrazol-1-one (r=1), perhydropyridazino[1,2-a]pyrazol-1-one (r=2) or perhydrodiazepino[1,2-a]pyrazolone (r=3) compound a6 crystallizes and is isolated by conventional methods of organic synthesis.

The final compound a7 in accordance with the present disclosure is obtained during reaction 5 by reducing the nitro derivative a6, wherein the methods of reduction used include, for example, hydrogenation by heterogeneous catalysis in the presence of Pd/C, Pd(II)/C, Ni/Ra, and the like or alternatively such as a reduction reaction with a metal, for example, zinc, iron, tin and the like (see *Advanced Organic Chemistry*, 3rd edition, J. March, 1985, Wiley Interscience and *Reduction in Organic Chemistry*, M. Hudlicky, 1983, Ellis Horwood Series Chemical Science).

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The following non-limiting examples serve to illustrate the invention.

EXAMPLES

Example 1

Synthesis of 2,3-diamino-6,7-dihydro-1H,5H-pyrazolo[1,2-a]pyrazol-1-one dihydrochloride 5

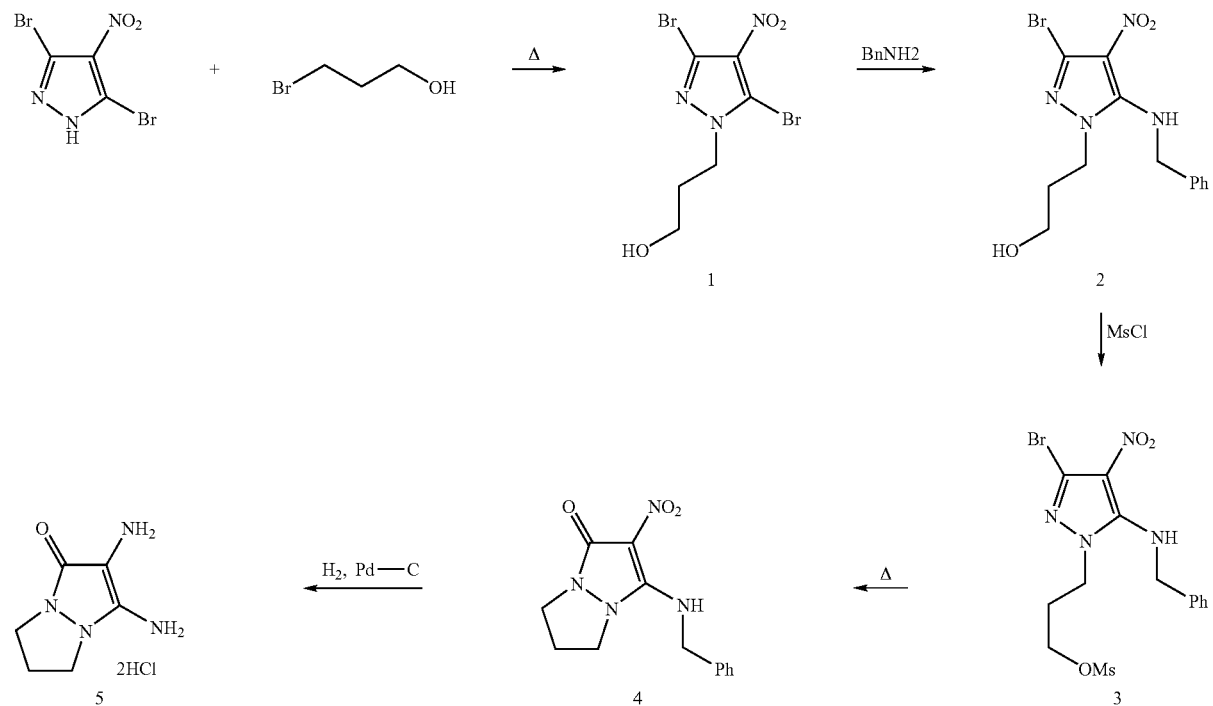

Reaction 1: Synthesis of 3-(3,5-dibromo-4-nitro-1H-pyrazol-1-yl)propan-1-ol 1

In a 500 ml three-necked flask, 0.369 mol of sodium acetate was introduced into a solution of 0.184 mol of dibromonitropyrazole in 250 ml of N-methylpyrrolidone and the reaction medium was heated to 80° C.

At this temperature, 0.369 mol of 3-bromopropanol was added dropwise. This temperature was maintained for 5 hours.

After cooling to room temperature, the medium was poured over ice, with stirring.

3-(3,5-Dibromo-4-nitro-1H-pyrazol-1-yl)propan-1-ol 1 precipitated. It was drained, dried and obtained with a yield of 75%.

The mass of the expected compound $C_6H_7Br_2N_3O_3$ was detected by mass spectrometry.

The NMR analyses ($^1H$ 400 MHz and $^{13}C$ 100.61 MHz DMSO $d_6$) are in conformity with the expected structure.

Reaction 2: Synthesis of 3-[5-(benzylamino)-3-bromo-4-nitro-1H-pyrazol-1-yl]propan-1-ol 2

0.135 mol of 3-(3,5-dibromo-4-nitro-1H-pyrazol-1-yl) propan-1-ol 1 was dispersed in a 500 ml three-necked flask containing 150 ml of ethanol, the medium was heated to 60° C. and then 0.825 mol of benzylamine was added over 30 minutes.

After 6 hours at 60° C., the reaction medium was cooled to room temperature.

3-[5-(Benzylamino)-3-bromo-4-nitro-1H-pyrazol-1-yl] propan-1-ol 2 was precipitated by pouring the reaction medium over 1 liter of ice, with stirring. After draining and drying under vacuum in the presence of $P_2O_5$, the compound 2 was isolated with a yield of 90%.

The NMR analyses ($^1H$ 400 MHz and $^{13}C$ 100.61 MHz DMSO $d_6$) are in conformity with the expected structure.

Elemental Analysis:

| | | | | |
|---|---|---|---|---|
| Theoretical: | C43.96 | H4.26 | N15.77 | O13.51 | Br22.50 |
| Measured: | C44.09 | H4.22 | N15.44 | O14.37 | Br21.50 |

Reaction 3: Synthesis of 3-[5-(benzylamino)-3-bromo-4-nitro-1H-pyrazol-1-yl]propyl methanesulphonate 3

0.126 mol of 3-[5-(benzylamino)-3-bromo-4-nitro-1H-pyrazol-1-yl]propan-1-ol 2 and 15.82 ml of triethylamine were introduced, with stirring, into a 500 ml three-necked flask containing 200 ml of THF. The mixture obtained was then cooled to 5° C. and 0.126 mol of mesyl chloride were poured in over 45 minutes.

The reaction medium was maintained at this temperature for 2 hours, and then 3-[5-(benzylamino)-3-bromo-4-nitro-1H-pyrazol-1-yl]propyl methanesulphonate 3 was precipitated by pouring the reaction medium over 800 ml of ice.

After filtration, the solid was thoroughly washed with water and with diisopropyl ether. Drying was carried out under vacuum in the presence of $P_2O_5$. The yield of this reaction was 94%.

The mass of the expected compound $C_{14}H_{17}BrN_4O_5S$ was detected by mass spectrometry.

The NMR analyses ($^1H$ 400 MHz and $^{13}C$ 100.61 MHz DMSO $d_6$) are in conformity with the expected structure.

Elemental Analysis:

| | | | | | |
|---|---|---|---|---|---|
| Theory: | C38.81 | H3.96 | N12.93 | O18.46 | S7.40 | Br18.44 |
| Measured: | C39.03 | H3.91 | N12.83 | O18.52 | S7.29 | Br18.26 |

Reaction 4: Synthesis of 3-(benzylamino)-2-nitro-6,7-dihydro-1H,5H-pyrazolo[1,2-a]pyrazol-1-one 4

0.1 mol of 3-[5-(benzylamino)-3-bromo-4-nitro-1H-pyrazol-1-yl]propyl methanesulphonate 3 was dispersed, with stirring, in a 500 ml three-necked flask containing 300 ml of pentanol and the reaction medium was heated at 130° C. for 2 hours.

After cooling to room temperature, the solid formed was drained on sintered glass, washed with diisopropyl ether and dried under vacuum in the presence of $P_2O_5$. 3-(Benzylamino)-2-nitro-6,7-dihydro-1H,5H-pyrazolo[1,2-a]pyrazol-1-one 4 was obtained with a yield of 86%.

The NMR analyses ($^1H$ 400 MHz and $^{13}C$ 100.61 MHz DMSO $d_6$) are in conformity with the expected structure.

The mass of the expected compound $C_6H_{11}N_4O$ was detected by mass spectrometry.

Elemental Analysis:

| | | | | |
|---|---|---|---|---|
| Theory: | C56.72 | H5.49 | N20.36 | O17.44 |
| Measured: | C56.68 | H5.13 | N20.38 | O17.69 |

Reaction 5: Synthesis of 2,3-diamino-6,7-dihydro-1H,5H-pyrazolo[1,2-a]pyrazol-1-one dihydrochloride 5

20 g of 3-(benzylamino)-2-nitro-6,7-dihydro-1H,5H-pyrazolo[1,2-a]pyrazol-1-one 4 and 4 g of 5% palladium on carbon were introduced into a 1 liter autoclave containing 800 ml of ethanol. The reduction was then carried out at a hydrogen pressure of 8 bar and at a temperature ranging from 50° C. to 100° C. (stirring with a speed ranging from 1000 to 2500 rpm).

After 4 hours of reaction, there was no further consumption of hydrogen and the medium was cooled to 20° C.

The catalyst was removed under nitrogen by filtration, and then hydrochloric ethanol was added to the filtrate. The crystallized product was drained, washed with diisopropyl ether and then dried under vacuum in the presence of $P_2O_5$. 2,3-Diamino-6,7-dihydro-1H,5H-pyrazolo[1,2-a]pyrazol-1-one dihydrochloride 5 was obtained with a yield of 89%.

The mass of the expected compound was detected by mass spectrometry.

The NMR analyses ($^1H$ 400 MHz and $^{13}C$ 100.61 MHz DMSO $d_6$) are in conformity with the expected structure.

Elemental Analysis:

| | | | | | |
|---|---|---|---|---|---|
| Theoretical: | C31.73 | H5.33 | N24.67 | O7.07 | Cl31.22 |
| Measured: | C31.45 | H5.20 | N24.62 | O7.24 | Cl30.86 |

Example 2

Synthesis of 2-amino-3-(ethylamino)-6,7-dihydro-1H,5H-pyrazolo[1,2-a]pyrazol-1-one dihydrochloride 9

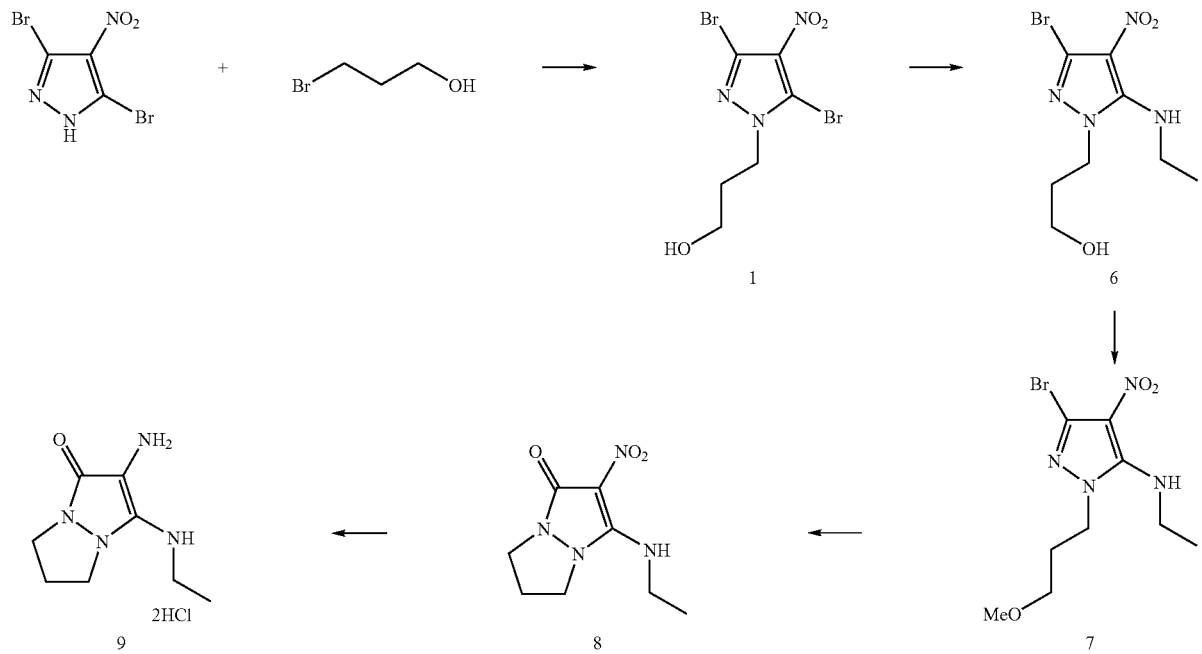

Reaction 2: Synthesis of 3-[3-bromo-5-(ethylamino)-4-nitro-1H-pyrazol-1-yl]propan-1-ol 6

15 mmol of 3-(3,5-dibromo-4-nitro-1H-pyrazol-1-yl)propan-1-ol in 30 ml of ethanol were introduced into a three-necked flask, with stirring. The homogeneous medium was heated to 75° C. and then 93 mmol of ethylamine were poured in dropwise and the stirring was maintained for four hours.

After cooling to room temperature, the medium was poured over ice and 3-[3-bromo-5-(ethylamino)-4-nitro-1H-pyrazol-1-yl]propan-1-ol 6 precipitated.

The yellow solid was drained, and then thoroughly washed with water and with diisopropyl ether. Drying was carried out under vacuum in the presence of $P_2O_5$. The mass recovered is 3.6 g.

The NMR analyses ($^1H$ 400 MHz and $^{13}C$ 100.61 MHz DMSO $d_6$) are in conformity with the expected structure.

The mass of the expected compound $C_8H_{13}BrN_4O_3$ was detected by mass spectrometry.

Reaction 3: Synthesis of 3-[5-(ethylamino)-3-bromo-4-nitro-1H-pyrazol-1-yl]propyl methanesulphonate 7

11.2 mmol of 3-[3-bromo-5-(ethylamino)-4-nitro-1H-pyrazol-1-yl]propan-1-ol 6 and 1.6 ml of triethylamine were introduced, with stirring, into a 100 ml three-necked flask containing 30 ml of THF. The orange-colored homogeneous mixture obtained was cooled to 0° C. and 1.44 ml of mesyl chloride were poured in over 20 minutes.

The reaction medium was maintained at this temperature for 2 hours and then 3-[5-(ethylamino)-3-bromo-4-nitro-1H-pyrazol-1-yl]propyl methanesulphonate 7 was precipitated by pouring the reaction medium over 500 ml of ice.

The yellow solid was drained, and then thoroughly washed with water and with diisopropyl ether; drying was carried out under vacuum in the presence of $P_2O_5$. The mass recovered is 3.1 g.

The NMR analyses ($^1H$ 400 MHz and $^{13}C$ 100.61 MHz DMSO $d_6$) are in conformity with the expected structure.

The mass of the expected compound $C_9H_{15}BrN_4O_5S$ was detected by mass spectrometry.

Reaction 4: Synthesis of 3-(ethylamino)-2-nitro-6,7-dihydro-1H,5H-pyrazolo[1,2-a]pyrazol-1-one 8

8 mmol of 3-[5-(ethylamino)-3-bromo-4-nitro-1H-pyrazol-1-yl]propyl methanesulphonate 7 were dispersed, with stirring, in a 50 ml three-necked flask containing 20 ml of pentanol, and the reaction medium was heated at 130° C. for 2 hours.

After cooling to room temperature, the solid formed was drained, and then washed with diisopropyl ether.

After drying under vacuum in the presence of $P_2O_5$, 1.46 g of 3-(ethylamino)-2-nitro-6,7-dihydro-1H,5H-pyrazolo[1,2-a]pyrazol-1-one 8 was obtained.

The NMR analyses ($^1H$ 400 MHz and $^{13}C$ 100.61 MHz DMSO $d_6$) are in conformity with the expected structure.

The mass of the expected compound was detected by mass spectrometry.

Reaction 5: Synthesis of 2-amino-3-(ethylamino)-6,7-dihydro-1H,5H-pyrazolo[1,2-a]pyrazol-1-one dihydrochloride 9

1.45 g of 3-(ethylamino)-2-nitro-6,7-dihydro-1H,5H-pyrazolo[1,2-a]pyrazol-1-one 8 and 300 mg of 5% palladium on carbon were introduced into a 300 ml autoclave containing 200 ml of ethanol. The reduction was carried out at a hydrogen pressure of 8 bar at a temperature of 60° C. (stirring at 1700 rpm).

After 2 hours of reaction, there was no further consumption of hydrogen and the medium was cooled to 20° C.

The catalyst was removed by filtration under nitrogen and the filtrate was diluted with 100 ml of hydrochloric isopropyl ether.

The pale yellow solution was evaporated to dryness and then the solid was taken up in an ethanol/isopropyl ether mixture. 2-Amino-3-(ethylamino)-6,7-dihydro-1H,5H-pyrazolo[1,2-a]pyrazol-1-one dihydrochloride 9 precipitated; it was drained and after drying under vacuum in the presence of $P_2O_5$, 1.18 g of 2-amino-3-(ethylamino)-6,7-dihydro-1H, 5H-pyrazolo[1,2-a]pyrazol-1-one dihydrochloride 9 were recovered.

The NMR analyses ($^1$H 400 MHz and $^{13}$C 100.61 MHz DMSO $d_6$) are in conformity with the expected structure.

The mass of the expected compound $C_8H_{14}N_4O$ was detected by mass spectrometry.

Example 3

2-amino-3-(isopropylamino)-6,7-dihydro-1H,5H-pyrazolo[1,2-a]pyrazol-1-one dihydrochloride 13

3-[3-bromo-5-(isopropylamino)-4-nitro-1H-pyrazol-1-yl]propan-1-ol 10 were obtained.

The NMR analyses ($^1$H 400 MHz and $^{13}$C 100.61 MHz DMSO $d_6$) are in conformity with the expected structure.

The mass of the expected compound $C_9H_{15}BrN_4O_3$ was detected by mass spectrometry.

Reaction 3: Synthesis of 3-[5-(isopropylamino)-3-bromo-4-nitro-1H-pyrazol-1-yl]propyl methanesulphonate 11

13.7 mmol of 3-[3-bromo-5-(isopropylamino)-4-nitro-1H-pyrazol-1-yl]propan-1-ol 10 and 1.94 ml of triethylamine were introduced, with stirring, into a 50 ml three-necked flask containing 20 ml of THF. The orange-colored homogeneous mixture thus obtained was cooled to 0° C. and 1.76 ml of mesyl chloride were poured in over 20 minutes.

The reaction medium was maintained at this temperature for 2 hours and then 3-[5-(ethylamino)-3-bromo-4-nitro-1H-pyrazol-1-yl]propyl methanesulphonate 11 was precipitated by pouring the reaction medium over 500 ml of ice.

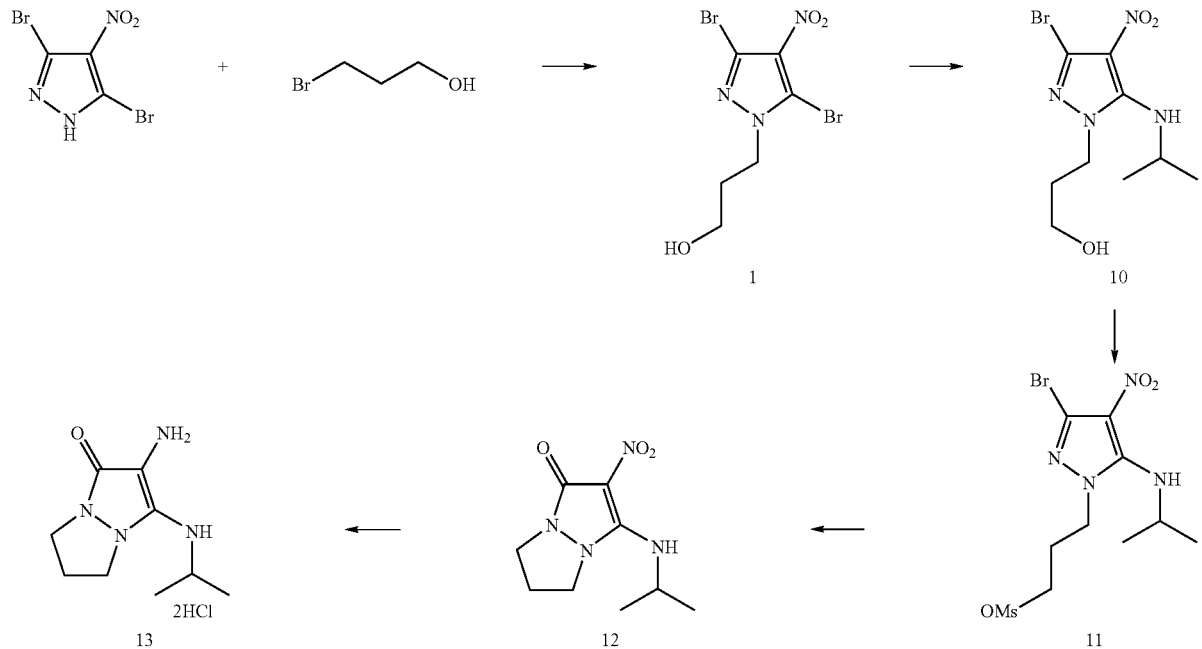

Reaction 2: 3-[3-bromo-5-(isopropylamino)-4-nitro-1H-pyrazol-1-yl]propan-1-ol 10

15 mmol of 3-(3,5-dibromo-4-nitro-1H-pyrazol-1-yl)propan-1-ol in 30 ml of ethanol were introduced into a three-necked flask, with stirring. The homogeneous medium was heated to 75° C., and then 93 mmol of isopropylamine were poured in dropwise while maintaining the stirring for four hours.

After cooling to room temperature, the medium was poured over ice, and then neutralized with hydrochloric acid. 3-[3-Bromo-5-(isopropylamino)-4-nitro-1H-pyrazol-1-yl]propan-1-ol 10 was extracted with dichloromethane.

After drying the organic phase over sodium sulphate and removing the solvent by evaporation under vacuum, 4.37 g of The yellow solid was drained and then thoroughly washed with water and petroleum ether, drying was carried out under vacuum in the presence of $P_2O_5$. The mass recovered is 4.2 g.

The NMR analyses ($^1$H 400 MHz and $^{13}$C 100.61 MHz DMSO $d_6$) are in conformity with the expected structure.

The mass of the expected compound was detected by mass spectrometry.

Reaction 4: Synthesis of 3-(isopropylamino)-2-nitro-6,7-dihydro-1H,5H-pyrazolo[1,2-a]pyrazol-1-one 12

10 mmol of 3-[5-(isopropylamino)-3-bromo-4-nitro-1H-pyrazol-1-yl]propyl methanesulphonate 11 in 20 ml of pentanol were dispersed, with stirring, in a 50 ml three-necked flask and the medium was heated at 130° C. for 2 hours.

After cooling to room temperature, the solid obtained was drained on sintered glass, and washed with diisopropyl ether.

After drying under vacuum in the presence of $P_2O_5$, 1.71 g of 3-(isopropylamino)-2-nitro-6,7-dihydro-1H,5H-pyrazolo[1,2-a]pyrazol-1-one 12 were obtained.

The NMR analyses ($^1$H 400 MHz and $^{13}$C 100.61 MHz DMSO $d_6$) are in conformity with the expected structure.

The mass of the expected compound $C_9H_{14}N_4O_3$ was detected by mass spectrometry.

The NMR analyses ($^1$H 400 MHz and $^{13}$C 100.61 MHz DMSO $d_6$) are in conformity with the expected structure.

The mass of the expected compound $C_9H_{16}N_4O$ was detected by mass spectrometry.

Example 4

2-amino-3-(pyrrolidin-1-yl)-6,7-dihydro-1H,5H-pyrazolo[1,2-a]pyrazol-1-one dihydrochloride 17

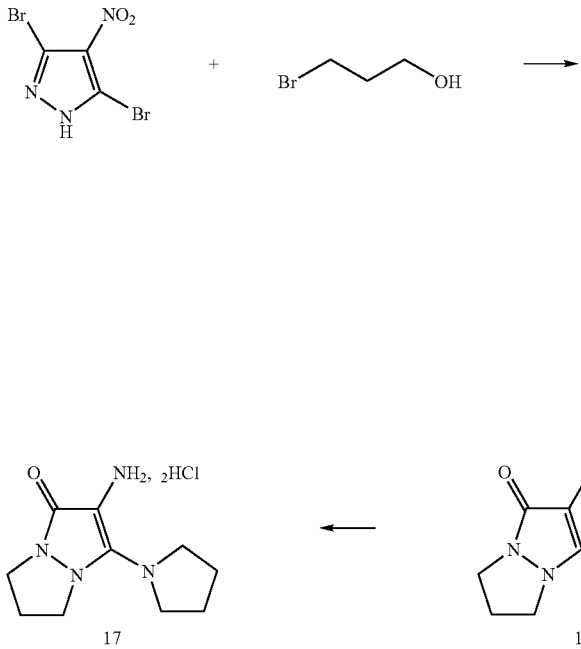
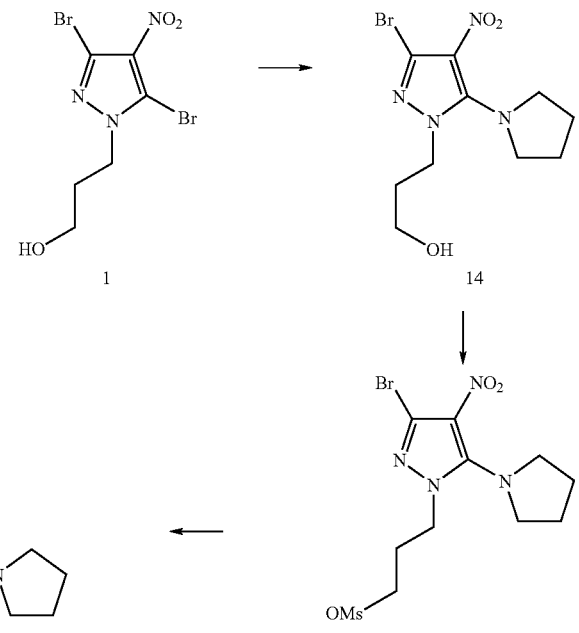

Reaction 5: Synthesis of 2-amino-3-(isopropylamino)-6,7-dihydro-1H,5H-pyrazolo[1,2-a]pyrazol-1-one dihydrochloride 13

1.70 g of 3-(isopropylamino)-2-nitro-6,7-dihydro-1H,5H-pyrazolo[1,2-a]pyrazol-1-one 12 and 300 mg of 5% palladium on carbon were introduced into a 300 ml autoclave containing 200 ml of ethanol. The reduction was carried out at a temperature of 60° C. and at a hydrogen pressure of 6 bar (stirring at 2000 rpm).

After 2 hours of reaction, there was no further consumption of hydrogen and the medium was cooled to 20° C.

The catalyst was removed by filtration under nitrogen after cooling to room temperature and hydrochloric isopropyl ether was added.

The pale yellow solution was evaporated to dryness and then the solid was taken up in 50 ml of diisopropyl ether saturated with hydrochloric acid, the precipitate was recovered by draining. After drying under vacuum in the presence of $P_2O_5$, 1.5 g of 2-amino-3-(isopropylamino)-6,7-dihydro-1H,5H-pyrazolo[1,2-a]pyrazol-1-one dihydrochloride 13 were isolated.

Reaction 2: 3-(3-bromo-4-nitro-5-(pyrrolidin-1-yl)-1H-pyrazol-1-yl)propan-1-ol 14

15 mmol of 3-(3,5-dibromo-4-nitro-1H-pyrazol-1-yl)propan-1-ol in 20 ml of isopropanol were introduced into a three-necked flask, with stirring. The homogeneous medium was heated to 75° C. and then 90 mmol of pyrrolidine were poured in dropwise and the stirring was maintained for 2 hours.

After cooling to room temperature, the medium was poured over ice and neutralized with hydrochloric acid. 3-(3-Bromo-4-nitro-5-(pyrrolidin-1-yl)-1H-pyrazol-1-yl)propan-1-ol 14 was extracted with dichloromethane.

After drying of the organic phase over sodium sulphate and distillation of the solvent by evaporation under vacuum, 4.8 g of 3-(3-bromo-4-nitro-5-(pyrrolidin-1-yl)-1H-pyrazol-1-yl)propan-1-ol 14 were obtained.

The NMR analyses ($^1$H 400 MHz and $^{13}$C 100.61 MHz DMSO $d_6$) are in conformity with the expected structure.

The mass of the expected compound $C_{10}H_{17}BrN_4O$ was detected by mass spectrometry.

Reaction 3: Synthesis of 3-(3-bromo-4-nitro-5-(pyrrolidin-1-yl)-1H-pyrazol-1-yl)propyl methanesulphonate 15

30 mmol of 3-(3-bromo-4-nitro-5-(pyrrolidin-1-yl)-1H-pyrazol-1-yl)propan-1-ol 14 and 4.25 ml of triethylamine were introduced, with stirring, into a 100 ml three-necked flask containing 50 ml of THF. The orange-colored homogeneous mixture obtained was cooled to 0° C. and 2.32 ml of mesyl chloride were poured in over 20 minutes.

The reaction medium was maintained at this temperature for 2 hours and then 3-(3-bromo-4-nitro-5-(pyrrolidin-1-yl)-1H-pyrazol-1-yl)propyl methanesulphonate 15 was precipitated by pouring the reaction medium over ice.

The solid was drained and then dried under vacuum in the presence of $P_2O_5$. The mass recovered is 9.3 g.

The NMR analyses ($^1$H 400 MHz and $^{13}$C 100.61 MHz DMSO $d_6$) are in conformity with the expected structure.

The mass of the expected compound $C_{11}H_{19}BrN_4O_3S$ was detected by mass spectrometry.

Reaction 4: Synthesis of 2-nitro-3-(pyrrolidin-1-yl)-6,7-dihydro-1H,5H-pyrazolo[1,2-a]pyrazol-1-one 16

22.5 mmol of 3-(3-bromo-4-nitro-5-(pyrrolidin-1-yl)-1H-pyrazol-1-yl)propyl methanesulphonate 15 in 100 ml of pentanol were introduced, with stirring, into a 250 ml three-necked flask. The medium thus obtained was heated at 130° C. for 2 hours.

After cooling to room temperature, 2-nitro-3-(pyrrolidin-1-yl)-6,7-dihydro-1H,5H-pyrazolo[1,2-a]pyrazol-1-one 16 was extracted with dichloromethane.

After drying of the organic phase over sodium sulphate and distillation of the solvent under vacuum, 1.2 g of 2-nitro-3-pyrrolidin-1-yl-6,7-dihydro-1H,5H-pyrazolo[1,2-a]pyrazol-1-one 16 were obtained.

The NMR analyses ($^1$H 400 MHz and $^{13}$C 100.61 MHz DMSO $d_6$) are in conformity with the expected structure.

The mass of the expected compound $C_{10}H_{14}N_4O_3$ was detected by mass spectrometry.

Reaction 5: Synthesis of 2-amino-3-(pyrrolidin-1-yl)-6,7-dihydro-1H,5H-pyrazolo[1,2-a]pyrazol-1-one dihydrochloride 17

1.1 g of 2-nitro-3-(pyrrolidin-1-yl)-6,7-dihydro-1H,5H-pyrazolo[1,2-a]pyrazol-1-one 16 and 300 mg of 5% palladium on carbon were introduced into a 300 ml autoclave containing 200 ml of ethanol. The reduction was carried out with stirring at 2000 rpm, at a temperature of 60° C. and at a hydrogen pressure of 6 bar.

After 2 hours of reaction, there was no further consumption of hydrogen and the medium was cooled to 20° C.

The catalyst was removed by filtration under nitrogen after cooling to room temperature and hydrochloric isopropyl ether was added.

The pale yellow solution was evaporated to dryness and then the solid was taken up in 50 ml of diisopropyl ether saturated with hydrochloric acid, the precipitate was recovered by draining. After drying under vacuum in the presence of $P_2O_5$, 1.5 g of 2-amino-3-(pyrrolidin-1-yl)-6,7-dihydro-1H,5H-pyrazolo[1,2-a]pyrazol-1-one dihydrochloride 17 were obtained.

The NMR analyses ($^1$H 400 MHz and $^{13}$C 100.61 MHz DMSO $d_6$) are in conformity with the expected structure.

The mass of the expected compound $C_{10}H_{16}N_4O$ was detected by mass spectrometry.

Example 5

Synthesis of 2,3-diamino-6,7,-dihydro-1H,5H-pyrazolo[1,2-a]pyrazol-1-one dimethanesulphonate

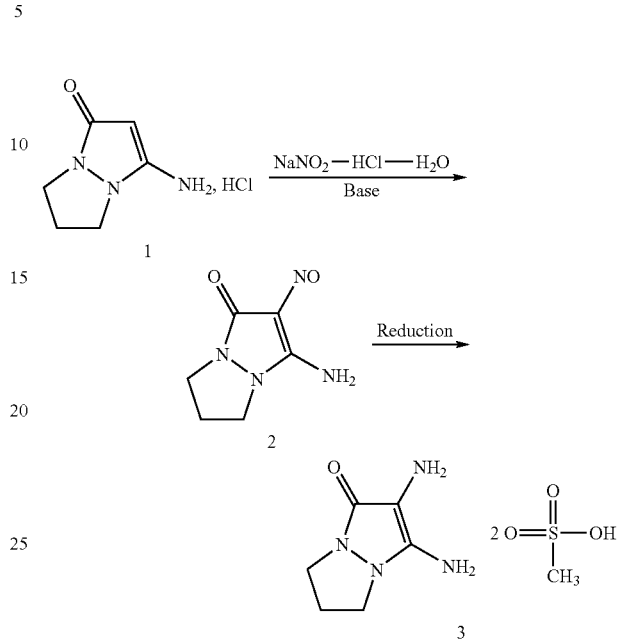

Synthesis of 3-amino-2-nitroso-6,7-dihydro-1H,5H-pyrazolo[1,2-a]pyrazol-1-one 2

In a 500 ml three-necked flask, 43 g (0.245 mol) of 3-amino-6,7-dihydro-1H,5H-pyrazolo[1,2-a]pyrazol-1-one hydrochloride were dissolved at room temperature, with stirring, in a mixture of 180 ml of water and 35 ml of 35% hydrochloric acid.

The medium was cooled to 0° C. and a solution of 17.3 g of sodium nitrite (0.25 mol) in 20 ml of water was added dropwise over 30 minutes. The temperature of the reaction medium was maintained in a range from 0 to +5° C. during the entire duration of the addition and for one hour after the end of the addition.

The reaction medium was brought to pH 8 by addition of sodium hydroxide, with stirring, while maintaining the temperature in a range from 0 to 5° C.

3-Amino-2-nitroso-6,7-dihydro-1H,5H-pyrazolo[1,2-a]pyrazol-1-one 2 precipitated in the form of a red-orange-colored solid which was filtered on No. 4 sintered glass, impasted in a minimum of 2-propanol, washed with diisopropyl ether and dried under vacuum in the presence of phosphorus pentoxide. 35 g of an orange-red product were thus obtained (yield: 85%).

The NMR spectra ($^1$H 400 MHz and $^{13}$C 100.61 MHz DMSO $d_6$) and mass spectra are in conformity with the expected structure 2.

Synthesis of 2,3-diamino-6,7-dihydro-1H,5H-pyrazolo[1,2-a]pyrazol-1-one dimethanesulphonate 3

33.6 g (0.2 mol) of 3-amino-2-nitroso-6,7-dihydro-1H,5H-pyrazolo[1,2-a]pyrazol-1-one 2, 500 ml of ethanol and 6 g of 5% palladium on carbon containing 50% of water were introduced into a 1 liter autoclave.

The medium was purged 3 times with nitrogen and then 3 times with hydrogen and the temperature of the mixture was brought to 40° C.

The reduction was carried out over two hours at a pressure of 8 bar. This reduction was exothermic and the temperature reached 70° C. by itself.

The temperature was allowed to decrease to 50° C. and then the catalyst was filtered on a filter press under a nitrogen stream.

The filtrate was poured into a mixture of 50 ml of ethanol and 40 ml of methanesulphonic acid, while cooling to 0° C. 2,3-Diamino-6,7-dihydro-1H,5H-pyrazolo[1,2-a]pyrazol-1-one dimethanesulphonate 3 crystallized in the form of a pale yellow solid which was drained on No. 4 sintered glass, washed with diisopropyl ether and then with petroleum ether, and finally dried under vacuum in the presence of phosphorus pentoxide. 43 g of a pale yellow solid were thus obtained (yield: 65%).

The NMR spectra ($^1$H 400 MHz and $^{13}$C 100.61 MHz DMSO $d_6$) and mass spectra are in conformity with the expected structure 3.

Elemental Analysis:

| Theory:   | C27.74 | H5.23 | N16.17 | O32.33 | S18.51 |
|-----------|--------|-------|--------|--------|--------|
| Measured: | C27.16 | H5.22 | N15.63 | O32.81 | S18.64 |

Example 6

Synthesis of 2,3-diamino-5,6,7,8-tetrahydro-1H-pyrazolo[1,2-a]pyridazin-1-one hydrochloride

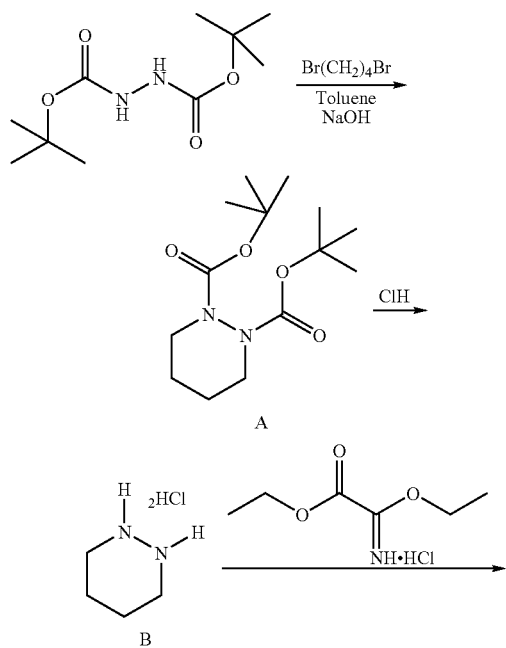

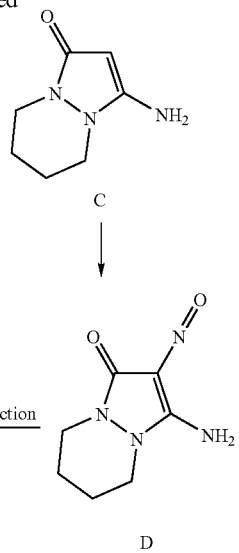

Synthesis of di-tert-butyl tetrahydropyridazine-1,2-dicarboxylate A 50 ml of toluene, 5 g (21.5 mmol) of N,N'-di-tert-butoxycarbonylhydrazide, 680 mg of tetraethylammonium bromide and 25 ml of 50% sodium hydroxide were introduced, with mechanical stirring, into a 250 ml three-necked flask equipped with a condenser, a thermometer and a dropping funnel.

The heterogeneous medium was heated to 100° C. and then 1,4-dibromobutane was added dropwise over 15 minutes.

The reaction medium was heated at 100° C. for 3 days. After cooling, 100 ml of ethyl acetate were added and the medium was transferred into a separating funnel. The organic phase was washed with 4×70 ml of a saturated aqueous sodium carbonate solution, and then with 4×70 ml of water and finally with 4×70 ml of salt water. The organic phase was dried over sodium sulphate and the solvent was evaporated under vacuum. A colorless oil was thus obtained which crystallized in the form of a white solid.

A mass of 6.1 g is recovered (yield: 99%).

The NMR spectra ($^1$H 400 MHz and $^{13}$C 100.61 MHz DMSO $d_6$) and mass spectra are in conformity with the expected structure A.

Synthesis of hexahydropyridazine dihydrochloride B 5.9 g of compound A in 50 ml of a 3/1 mixture of dioxane and 35% hydrochloric acid were introduced, with mechanical stirring, into a 100 ml three-necked flask equipped with a condenser and a thermometer.

The colorless solution obtained was stirred at room temperature for 3 hours and then the reaction medium was diluted with diisopropyl ether. The solvents were evaporated under vacuum. The pasty residue obtained was taken up in an ether/ethanol mixture. After filtration of the solid and drying under vacuum, 1.39 g of a white solid were obtained.

The NMR spectra ($^1$H 400 MHz and $^{13}$C 100.61 MHz DMSO $d_6$) and mass spectra are in conformity with the expected structure B.

Synthesis of 3-amino-5,6,7,8-tetrahydro-1H-pyrazolo[1,2-a]pyridazin-1-one C 7.5 ml of ethanol, 1.5 ml of triethylamine and 0.73 ml of 3-amino-3-ethoxyacrylic acid were introduced, with mechanical stirring, into a 25 ml three-necked flask equipped with a condenser and a thermometer. 500 mg of hexahydropyridazine dihydrochloride (compound B) were then added and the medium was stirred for 3 hours at room temperature.

The insoluble material was filtered and the solvent was distilled under vacuum. The solid was taken up in a minimum of water, filtered and dried under vacuum. 0.9 g of a slightly yellow powder was obtained.

The NMR spectra ($^1$H 400 MHz and $^{13}$C 100.61 MHz DMSO $d_6$) and mass spectra are in conformity with the expected structure C.

Synthesis of 3-amino-2-nitroso-5,6,7,8-tetrahydro-1H-pyrazolo[1,2-a]pyridazin-1-one D 20 ml of hydrochloric acid at 35% and 1 g of 3-amino-5,6,7,8-tetrahydro-1H-pyrazolo[1,2-a]pyridazin-1-one (compound C) were introduced, with mechanical stirring, into a 50 ml three-necked flask equipped with a condenser and a thermometer.

The medium was cooled to 0° C. and a solution of 675 mg of sodium nitrite in 5 ml of water was poured in while maintaining this temperature. The color of the reaction mixture changes from yellow to orange and a precipitate began to form.

Within 30 minutes, the reaction was complete and the orange solid was filtered on No. 4 sintered glass, washed with water and then dried under vacuum. The yield is 78.3%.

The NMR spectra ($^1$H 400 MHz and $^{13}$C 100.61 MHz DMSO $d_6$) and mass spectra are in conformity with the expected structure D.

Synthesis of 2,3-diamino-5,6,7,8-tetrahydro-1H-pyrazolo[1,2-a]pyridazin-1-one hydrochloride E 1.3 g of 3-amino-2-nitroso-5,6,7,8-tetrahydro-1H-pyrazolo[1,2-a]pyridazin-1-one (compound D) and 250 mg of 5% palladium on carbon were introduced into a 300 ml autoclave containing 250 ml of ethanol. The reduction was carried out with stirring at 2000 rpm, at a temperature of 60° C. and at a hydrogen pressure of 6 bar. At the end of 2 hours of reaction, there was no further consumption of hydrogen and the medium was cooled to 20° C.

The catalyst was removed by filtration under nitrogen after cooling to room temperature and the solution was poured over 75 ml of hydrochloric dioxane.

The solution thus obtained was evaporated until a slightly yellow powder was obtained which was recovered in diisopropyl ether.

The solid was recovered by filtration. After drying under vacuum in the presence of phosphorus pentoxide, 1.1 g of 2,3-diamino-5,6,7,8-tetrahydro-1H-pyrazolo[1,2-a]pyridazin-1-one hydrochloride were obtained.

The NMR spectra ($^1$H 400 MHz and $^{13}$C 100.61 MHz DMSO $d_6$) and mass spectra are in conformity with the expected structure E.

EXAMPLES OF DYE

Examples 1 to 3

Dye in an acidic medium using 2,3-diamino-6,7-dihydro-1H,5H-pyrazolo[1,2-a]pyrazol-1-one The following dyeing compositions were prepared:

|  | Example | | |
| --- | --- | --- | --- |
|  | 1 | 2 | 3 |
| 2,3-Diamino-6,7-dihydro-1H,5H-pyrazolo[1,2-a]pyrazol-1-one dihydrochloride | $10^{-3}$ mol | $10^{-3}$ mol | $10^{-3}$ mol |
| 5-Amino-2-methylphenol | $10^{-3}$ mol | | |
| 2-(2,4-Diaminophenoxy)ethanol, hydrochloride | | $10^{-3}$ mol | |
| 3-Amino-2-chloro-6-methylphenol, hydrochloride | | | $10^{-3}$ mol |
| Dye carrier (1) | (*) | (*) | (*) |
| Demineralized water q.s. | 100 g | 100 g | 100 g |

(*): dye carrier (1) pH 7

| | | |
| --- | --- | --- |
| Ethyl alcohol at 96% | 20.8 g | |
| Sodium metabisulphite as an aqueous solution at 35% | 0.23 g | A.M. |
| Pentasodium salt of diethylene-triaminepentaacetic acid as an aqueous solution at 40% | 0.48 g | A.M. |
| $C_8$-$C_{10}$ alkyl polyglucoside as an aqueous solution at 60% | 3.6 g | A.M. |
| Benzyl alcohol | 2.0 g | |
| Polyethylene glycol containing 8 ethylene oxide units | 3.0 g | |
| $Na_2HPO_4$ | 0.28 g | |
| $KH_2PO_4$ | 0.46 g | |

"A.M." means active material.

At the time of use, each composition was mixed with an equal weight of hydrogen peroxide at 20 volumes (6% by weight). A final pH of 7 was obtained.

Each mixture obtained was applied to locks of grey hair which were 90% white. After an exposure time of 30 minutes, the locks were rinsed, washed with a standard shampoo, rinsed again and then dried.

The shades obtained are presented in the table below:

|  | Example | | |
| --- | --- | --- | --- |
|  | 1 | 2 | 3 |
| Shade observed | chromatic orange | intense chromatic red | chromatic orange |

Examples 4 to 6

Dye in an alkaline medium using 2,3-diamino-6,7-dihydro-1H,5H-Pyrazolo[1,2-a]pyrazol-1-one The following dyeing compositions were prepared:

|  | Example | | |
| --- | --- | --- | --- |
|  | 4 | 5 | 6 |
| 2,3-Diamino-6,7-dihydro-1H,5H-pyrazolo[1,2-a]pyrazol-1-one dihydrochloride | $10^{-3}$ mol | $10^{-3}$ mol | $10^{-3}$ mol |

-continued

| | Example | | |
|---|---|---|---|
| | 4 | 5 | 6 |
| 5-Amino-2-methylphenol | $10^{-3}$ mol | | |
| 2-(2,4-Diaminophenoxy)ethanol, hydrochloride | | $10^{-3}$ mol | |
| 3-Amino-2-chloro-6-methylphenol, hydrochloride | | | $10^{-3}$ mol |
| Dye carrier (2) | (*) | (*) | (*) |
| Demineralized water q.s. | 100 g | 100 g | 100 g |

(*): dye carrier (2) pH 9.5

| | | |
|---|---|---|
| Ethyl alcohol at 96% | 20.8 g | |
| Sodium metabisulphite as an aqueous solution at 35% | 0.23 g | A.M. |
| Pentasodium salt of diethylene-triaminepentaacetic acid as an aqueous solution at 40% | 0.48 g | A.M. |
| $C_8$-$C_{10}$ alkyl polyglucoside as an aqueous solution at 60% | 3.6 g | A.M. |
| Benzyl alcohol | 2.0 g | |
| Polyethylene glycol containing 8 ethylene oxide units | 3.0 g | |
| $NH_4Cl$ | 4.32 g | |
| Ammonium hydroxide containing 20% of $NH_3$ | 2.94 g | |

"A.M." means active material.

At the time of use, each composition was mixed with an equal weight of hydrogen peroxide at 20 volumes (6% by weight). A final pH of 9.5 was obtained.

Each mixture obtained was applied to locks of grey hair which were 90% white. After an exposure time of 30 minutes, the locks were rinsed, washed with a standard shampoo, rinsed again and then dried.

The shades obtained are presented in the table below:

| | Example | | |
|---|---|---|---|
| | 4 | 5 | 6 |
| Shade observed | chromatic orange | chromatic red | chromatic orange |

What is claimed is:

1. A method for preparing a compound of formula (I):

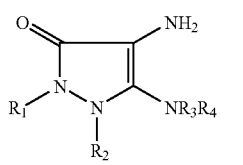

(I)

wherein:
$R_1$, $R_2$, $R_3$ and $R_4$, which are identical or different, are each chosen from:
linear and branched 01-06 alkyl radicals optionally substituted with at least one radical chosen from a radical $OR_5$, a radical $NR_6R_7$, a carboxyl radical, a sulphonic radical, a carboxamido radical $CONR_6R_7$, a sulphonamido radical $SO_2NR_6R_7$, heteroaryl radicals, and aryl radicals optionally substituted with at least one radical chosen from $(C_1$-$C_4)$alkyl, hydroxyl, $C_1$-$C_2$ alkoxy, amino, and (di)alkyl$(C_1$-$C_2)$amino radicals;
aryl radicals optionally substituted with at least one radical chosen from $(C_1$-$C_4)$alkyl, hydroxyl, $C_1$-$C_2$ alkoxy, amino, and (di)alkyl$(C_1$-$C_2)$amino radicals; and
5- and 6-membered heteroaryl radicals optionally substituted with at least one radical chosen from $(C_1$-$C_4)$alkyl and $(C_1$-$C_2)$alkoxy radicals;
or alternatively, $R_3$ and $R_4$ are each a hydrogen atom;
$R_5$, $R_6$ and $R7$, which are identical or different, are each chosen from a hydrogen atom; linear and branched $C_1$-$C_4$ alkyl radicals optionally substituted with at least one radical chosen from a hydroxyl radical, $C_1$-$C_2$ alkoxy radicals, a carboxamido radical $CONR_8R_9$, a sulphonyl radical $SO_2R_8$, and aryl radicals optionally substituted with at least one radical chosen from $(C_1$-$C_4)$alkyl, hydroxyl, $C_1$-$C_2$ alkoxy, amino, and (di)alkyl$(C_1$-$C_2)$amino radicals; and aryl radicals optionally substituted with at least one radical chosen from $(C_1$-$C_4)$alkyl, hydroxyl, $C_1$-$C_2$ alkoxy, amino, and (di)alkyl$(C_1$-$C_2)$ amino radicals;
or alternatively $R_6$ and $R_7$, which are identical or different, are each chosen from a carboxamido radical $CONR_8R_9$ and a sulphonyl radical $SO_2R_8$;
$R_8$ and $R_9$, which are identical or different, are each chosen from a hydrogen atom; and linear and branched $C_1$-$C_4$ alkyl radicals optionally substituted with at least one radical chosen from hydroxyl and $C_1$-$C_2$ alkoxy radicals;
wherein at least one of $R_1$ and $R_2$, and $R_3$ and $R_4$, may form, together with the nitrogen atoms to which they are attached, a heterocycle chosen from saturated and unsaturated 5- to 7-membered heterocycles optionally substituted with at least one entity chosen from halogen atoms and amino, (di)alkyl $C_1$-$C_4$)amino, hydroxyl, carboxyl carboxamido and $C_1$-$C_2$)alkoxy radicals, and $C_1$-$C_4$ alkyl radicals optionally substituted with at least one radical chosen from hydroxyl, amino, (di)alkylamino, alkoxy, carboxyl and sulphonyl radicals; and
$R_3$ and $R_4$ may also form, together with the nitrogen atom to which they are attached, a 5- or 7-membered heterocycle whose carbon atoms are optionally replaced with at least one optionally substituted atom chosen from optionally substituted oxygen and nitrogen atoms,
said method comprising:
a) reaction 1: reacting a compound a

    a with a compound b:

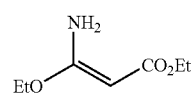    b to give a compound 5-amino-1, 2-dihydropyrazol-3-one c:

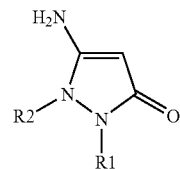    c b) reaction 2: reacting the derivative c thus obtained with an aryldiazonium salt (Ar—N$_2^\oplus$Y$^\ominus$) to give an azo compound f:

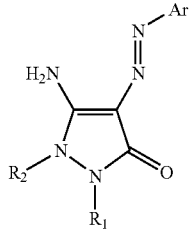

f c) reaction 3: optionally functionalizing the primary amine group of the resulting azo compound f to give the following compound g:

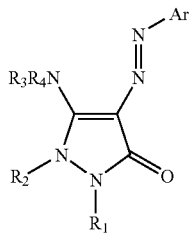

g d) reaction 4: carrying out a reaction of reduction of the azo compound f or g to obtain an amine-containing compound e or h respectively:

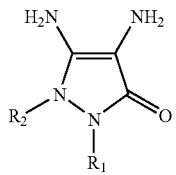

e

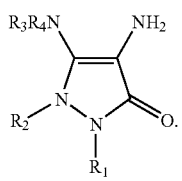

h

2. A method for preparing a compound of formula (I):

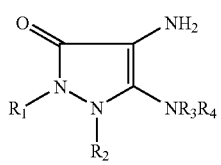

(I)

wherein:

$R_1$, $R_2$, $R_3$ and $R_4$, which are identical or different, are each chosen from:

linear and branched $C_1$-$C_6$ alkyl radicals optionally substituted with at least one radical chosen from a radical $OR_5$, a radical $NR_6R_7$, a carboxyl radical, a sulphonic radical, a carboxamido radical $CONR_6R_7$, a sulphonamido radical $SO_2NR_6R_7$, heteroaryl radicals, and aryl radicals optionally substituted with at least one radical chosen from ($C_1$-$C_4$)alkyl, hydroxyl, $C_1$-$C_2$ alkoxy, amino, and (di)alkyl($C_1$-$C_2$)amino radicals;

aryl radicals optionally substituted with at least one radical chosen from ($C_1$-$C_4$)alkyl, hydroxyl, $C_1$-$C_2$ alkoxy, amino, and (di)alkyl($C_1$-$C_2$)amino radicals; and 5- and 6-membered heteroaryl radicals optionally substituted with at least one radical chosen from ($C_1$-$C_4$)alkyl and ($C_1$-$C_4$)alkoxy radicals;

or alternatively, $R_3$ and $R_4$ are each a hydrogen atom;

$R_5$, $R_6$ and $R_7$, which are identical or different, are each chosen from a hydrogen atom; linear and branched $C_1$-$C_4$ alkyl radicals optionally substituted with at least one radical chosen from a hydroxyl radical, $C_1$-$C_2$ alkoxy radicals, a carboxamido radical $CONR_8R_9$, a sulphonyl radical $SO_2R_8$, and aryl radicals optionally substituted with at least one radical chosen from ($C_1$-$C_4$)alkyl, hydroxyl, $C_1$-$C_2$ alkoxy, amino, and (di)alkyl($C_1$-$C_2$)amino radicals; and aryl radicals optionally substituted with at least one radical chosen from ($C_1$-$C_4$)alkyl, hydroxyl, $C_1$-$C_2$ alkoxy, amino, and (di)alkyl($C_1$-$C_2$) amino radicals;

or, alternatively, $R_6$ and $R_7$, which are identical or different, are each chosen from a carboxamido radical $CONR_8R_9$ and a sulphonyl radical $SO_2R_8$;

$R_8$ and $R_9$, which are identical or different, are each chosen from a hydrogen atom; and linear and branched $C_1$-$C_4$ alkyl radicals optionally substituted with at least one radical chosen from hydroxyl and $C_1$-$C_2$ alkoxy radicals;

wherein at least one of $R_1$ and $R_2$, and $R_3$ and $R_4$, may form, together with the nitrogen atoms to which they are attached, a heterocycle chosen from saturated and unsaturated 5- to 7-membered heterocycles optionally substituted with at least one entity chosen from halogen atoms and amino, (di)alkyl($C_1$-$C_4$)amino, hydroxyl, carboxyl carboxamido and ($C_1$-$C_2$)alkoxy radicals, and $C_1$-$C_4$ alkyl radicals optionally substituted with at least one radical chosen from hydroxyl, amino, (di)alkylamino, alkoxy, carboxyl and sulphonyl radicals; and $R_3$ and $R_4$ may also form, together with the nitrogen atom to which they are attached, a 5- or 7-membered heterocycle whose carbon atoms are optionally replaced with at least one optionally substituted atom chosen from optionally substituted oxygen and nitrogen atoms, comprising:

a) reaction 1: reacting the following compound a1:

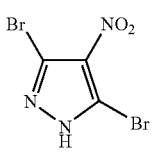

a1 with a compound a2:

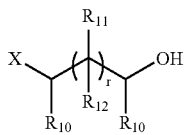

a2 to give a compound a3:

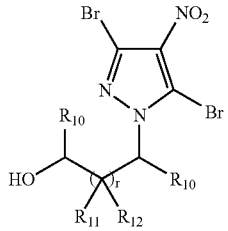

a3 wherein:

$R_{10}$ is chosen from a hydrogen atom, a carboxyl radical, a carboxamido radical; and $C_1$-$C_4$ alkyl radicals optionally substituted with at least one radical chosen from hydroxyl, amino, (di)alkylamino, alkoxy, carboxyl and sulphonyl radicals;

$R_{11}$ and $R_{12}$, which are identical or different, are each chosen from hydrogen and halogen atoms; an amino radical; (di)alkyl($C_1$-$C_4$)amino radicals; a hydroxyl radical; a carboxyl radical; a carboxamido radical; ($C_1$-$C_2$)alkoxy radicals; $C_1$-$C_4$ alkyl radicals optionally substituted with at least one radical chosen from hydroxyl, amino, (di)alkylamino, alkoxy, carboxyl and sulphonyl radicals;

X is chosen from halogen atoms and alkyl sulphonates;

r is an integer ranging from 1 to 3;

b) reaction 2: reacting the compound a3 with an amine of formula $NHR_3R_4$ to give a compound a4:

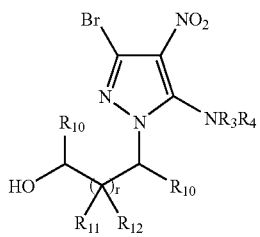

a4 c) reaction 3: reacting the compound a4 with at least one compound chosen from alkylsulphonyl, arylsulphonyl and perfluoroalkylsulphonyl halides R—O$_2$S—X$_1$, wherein R is chosen from alkyl, aryl and perfluoroalkyl radicals, and X$_1$ is chosen from halogen atoms, in an aprotic solvent in order to give a compound a5:

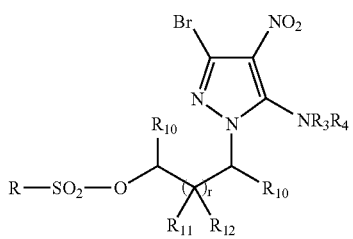

a5 d) reaction 4: heating the resulting compound a5 in a solvent having a boiling point ranging from 60° C. to 190° C. to give a compound a6:

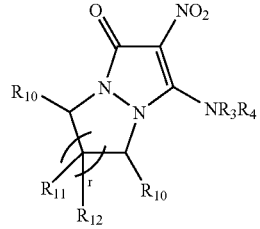

a6 e) reaction 5: reducing the compound a6 obtained to give the compound a7 of formula (III) below:

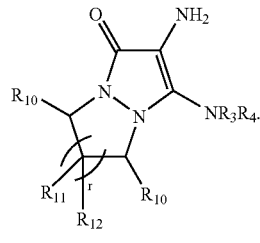

formula (III)

a7

3. The method according to claim 1, wherein $R_1$ and $R_2$ are chosen from $C_1$-$C_4$ alkyl radicals optionally substituted with at least one radical chosen from hydroxyl, ($C_1$-$C_2$)alkoxy, amino, and (di)alkyl($C_1$-$C_2$)amino radicals; and a phenyl radical.

4. The method according to claim 3, wherein $R_1$ and $R_2$ are chosen from methyl, ethyl, 2-hydroxyethyl, 3-hydroxypropyl, 2-hydroxypropyl and phenyl radicals.

5. The method according to claim 1, wherein $R_1$ and $R_2$ form, together with the nitrogen atoms to which they are attached, a ring chosen from saturated and unsaturated optionally substituted 5- and 6-membered rings.

6. The method according to claim 1, wherein $R_1$ and $R_2$ form, together with the nitrogen atoms to which they are attached, a pyrazolidine or pyridazolidine ring optionally substituted with at least one radical chosen from $C_1$-$C_4$ alkyl, hydroxyl, ($C_1$-$C_2$)alkoxy, carboxyl, carboxamido, amino, and (di)alkyl($C_1$ -$C_2$)amino radicals.

7. The method according to claim 1, wherein $R_1$ and $R_2$ form, together with the nitrogen atoms to which they are attached, a pyrazolidine or pyridazolidine ring.

8. The method according to claim 1, wherein $R_3$ and R4 are chosen from a hydrogen atom; linear and branched $C_1$-$C_4$ alkyl radicals optionally substituted with at least one radical chosen from hydroxyl, ($C_1$-$C_2$)alkoxy, amino, and (di)alkyl($C_1$-$C_2$)amino radicals; and a phenyl radical optionally substituted with at least one radical chosen from hydroxyl, amino and ($C_1$-$C_2$)alkoxy radicals.

9. The method according to claim 1, wherein $R_3$ and $R_4$ are chosen from a hydrogen atom, and methyl, ethyl, isopropyl, 2-hydroxyethyl, 3-hydroxypropyl, 2-hydroxypropyl and 2-carboxyethyl radicals.

10. The method according to claim 9, wherein $R_3$ and $R_4$ are each a hydrogen atom.

11. The method according to claim 1, wherein $R_3$ and $R_4$ form, together with the nitrogen atom to which they are attached, a 5- or 7-membered ring chosen from pyrrolidine, piperidine, homopiperidine, piperazine and homopiperazine heterocycles; wherein said ring is optionally substituted with at least one radical chosen from hydroxyl, amino,(di)alkyl $(C_1-C_2)$amino, carboxyl and carboxamido radicals, and $C_1-C_4$ alkyl radicals optionally substituted with at least one radical chosen from hydroxyl, amino, and $C_1-C_2$(di)alkylamino radicals.

12. The method according to claim 1, wherein $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)-pyrrolidine, 2-hydroxymethylpyrrolidine, 3,4-dihydroxy-2-hydroxymethylpyrrolidine,3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine,3-hydroxymethylpiperidine, homopiperidine, 2-carboxyhomopiperidine, 2-carboxamidohomopiperidine, homopiperazine, N-methylhomopiperazine, and N-(2-hydroxyethyl)homopiperazine.

13. The method according to claim 1, wherein $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine, and N-β-hydroxyethylhomopiperazine.

14. The method according to claim 1, wherein $R_3$ and $R_4$ form, together with the nitrogen atom to which they are attached, a 5-membered ring.

15. The method according to claim 14, wherein the 5-membered ring is chosen from pyrrolidine, 3-hydroxypyrrolidine, 3aminopyrrolidine, and 3-dimethylaminopyrrolidine.

16. The method according to claim 1, wherein the diamino-N,N-dihydropyrazolone compounds of formula (I) and the addition salts thereof are chosen from 4,5-diamino-1,2-dimethyl- 1,2-dihydropyrazol-3-one,
4-amino-5-methylamino-1,2-dimethyl-1,2-dihydropyrazol-3-one,
4-amino-5-dimethylamino-1,2-dimethyl-1,2-dihydropyrazol-3-one,
4-amino-5-(2-hydroxyethyl)amino-1,2-dimethyl- 1,2-dihydropyrazol-3-one,
4-amino-5-(pyrrolidin-1-yl)-1,2-dimethyl-1,2-dihydropyrazol-3-one,
4-amino-5-(piperidin-1 -yl)-1,2-dimethyl-1,2-dihydropyrazol-3-one,
4, 5-diamino-1,2-di(2-hydroxyethyl)-1,2-dihydropyrazol-3-one,
4-amino-5-methylamino-1,2-di(2-hydroxyethyl)-1,2-dihydropyrazol-3-one,
4-amino-5-dimethylamino-1,2-di(2-hydroxyethyl)-1,2-dihydropyrazol-3-one,
4-amino-5-(2-hydroxyethyl)amino-1,2-di(2-hydroxyethyl)- 1,2-dihydropyrazol-3-one,
4-amino-5-(pyrrolidin-1-yl)-1,2-di(2-hydroxyethyl)-1,2-dihydropyrazol-3-one,
4-amino-5-(piperidin-1-yl)-1,2-di(2-hydroxyethyl)-1,2-dihydropyrazol-3-one,
4,5-diamino-1,2-diethyl-1 ,2-dihydropyrazol-3-one,
4,5-diamino-1,2-phenyl-1,2-dihydropyrazol-3-one,
4,5-diamino-1-ethyl-2-methyl-1,2-dihydropyrazol-3-one,
4,5-diamino-2-ethyl-1-methyl-1,2-dihydropyrazol-3-one,
4,5-diamino-1-phenyl-2-methyl-1,2-dihydropyrazol-3-one,
4,5-diamino-1-(2-hydroxyethyl)-2-methyl-1,2-dihydropyrazol-3-one,
4,5-diamino-2-(2-hydroxyethyl)-1-methyl-1,2-dihydropyrazol-3-one,
2,3-diamino-6,7-dihydro-1H,5H-pyrazolo[1,2-a]pyrazol-1-one,
2-amino-3-methylamino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-(2-hydroxyethyl)amino-6,7-dihydro-1H,5H-pyrazolo[1,2-a]pyrazol-1-one,
2-amino-3-(2-hydroxypropyl)amino-6,7-dihydro-1H,5H-pyrazolo[1,2-a]pyrazol-1-one,
2-amino-3-bis(2-hydroxyethyl)amino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one,
2-amino-3-(3-hydroxypyrrolidin-1-yl)-6,7-dihydro-1H,5H-pyrazolo[1,2-a]pyrazol-1-one,
2-amino-3-(piperidin-1-yl)-6,7-dihydro-1H,5H-pyrazolo[1,2-a]pyrazol-1-one,
2,3-diamino-6-hydroxy-6,7-dihydro-1H,5H-pyrazolo[1,2-a]pyrazol-1-one,
2,3-diamino-6-methyl-6,7-dihydro-1H,5H-pyrazolo[1,2-a]pyrazol-1-one,
2,3-diamino-6-dimethyl-6,7-dihydro-1H,5H-pyrazolo[1,2-a]pyrazol-1-one,
2,3-diamino-5,6,7,8-tetrahydro-1H,6H-pyridazino[1,2-a]pyrazol-1-one, and
2,3-diamino-5,8-dihydro-1H,6H-pyridazino[1,2-a]pyrazol-1-one.

17. The method according to claim 1, wherein the diamino-N,N-dihydropyrazolone compounds of formula (I) and the addition salts thereof are chosen from 4,5-diamino-1,2-dimethyl-1,2-dihydropyrazol-3-one,
4,5-diamino-1,2-diethyl-1,2-dihydropyrazol-3-one,
4,5-diamino-1,2-di(2-hydroxyethyl)-1,2-dihydropyrazol-3-one,
2,3-diamino-6,7-dihydro-1H,5H-pyrazolo[1,2-a]pyrazol-1-one,
2-amino-3-isopropylamino-6,7-dihydro-1H,5H-pyrazolo[1,2-a]pyrazol-1-one,
2-amino-3-ethylamino-6,7-dihydro-1H,5H-pyrazolo[1,2-a]pyrazol-1-one,
2-amino-3-(2-hydroxyethyl)amino-6,7-dihydro-1H,5H-pyrazolo[1,2-a]pyrazol-1-one,
2-amino-3-dimethylamino-6,7-dihydro-1H,5H-pyrazolo[1,2-a]pyrazol-1-one,
2-amino-3-(pyrrolidin-1-yl)-6,7-dihydro-1H,5H-pyrazolo[1,2-a]pyrazol-1-one, and
2,3-diamino-5,6,7,8-tetrahydro-1H,6H-pyridazino[1,2-a]pyrazol-1-one.

* * * * *

UNITED STATES PATENT AND TRADEMARK OFFICE
CERTIFICATE OF CORRECTION

PATENT NO. : 7,642,360 B2  Page 1 of 1
APPLICATION NO. : 11/898438
DATED : January 5, 2010
INVENTOR(S) : Laurent Vidal et al.

It is certified that error appears in the above-identified patent and that said Letters Patent is hereby corrected as shown below:

Claim 1, col. 39, line 57, "01-06 alkyl" should read -- $C_1$-$C_6$ alkyl --.

Claim 1, col. 40, line 5, "R7" should read -- $R_7$ --.

Claim 1, col. 40, line 30, "$C_1$-$C_4$)" should read -- ($C_1$-$C_4$) --.

Claim 1, col. 40, line 31, "$C_1$-$C_2$)" should read -- ($C_1$-$C_2$) --.

Claim 2, col. 42, line 15, "($C_1$-$C_4$) alkoxy" should read -- ($C_1$-$C_2$) alkoxy --.

Signed and Sealed this

Sixth Day of April, 2010

David J. Kappos
*Director of the United States Patent and Trademark Office*